US007125888B2

(12) United States Patent
Bilodeau et al.

(10) Patent No.: US 7,125,888 B2
(45) Date of Patent: Oct. 24, 2006

(54) TYROSINE KINASE INHIBITORS

(75) Inventors: Mark T. Bilodeau, Lansdale, PA (US); Mark E. Fraley, North Wales, NJ (US); Zhicai Wu, Quakertown, PA (US)

(73) Assignee: Merck & Co., Inc., Rahway, NJ (US)

( * ) Notice: Subject to any disclaimer, the term of this patent is extended or adjusted under 35 U.S.C. 154(b) by 35 days.

(21) Appl. No.: 10/512,927

(22) PCT Filed: Apr. 28, 2003

(86) PCT No.: PCT/US03/13353

§ 371 (c)(1),
(2), (4) Date: Oct. 29, 2004

(87) PCT Pub. No.: WO03/092595

PCT Pub. Date: Nov. 13, 2003

(65) Prior Publication Data

US 2005/0176753 A1  Aug. 11, 2005

Related U.S. Application Data

(60) Provisional application No. 60/377,502, filed on May 2, 2002.

(51) Int. Cl.
A61K 31/535 (2006.01)
A61K 31/5513 (2006.01)
A61K 31/4375 (2006.01)
C07D 407/04 (2006.01)

(52) U.S. Cl. ............ 514/300; 514/300; 514/218; 514/231.5; 514/253.04; 544/362; 544/106; 540/489; 546/121

(58) Field of Classification Search ............ 546/121; 514/300
See application file for complete search history.

(56) References Cited

U.S. PATENT DOCUMENTS

| 3,734,923 A | 5/1973 | Dowding et al. |
| 3,755,347 A | 8/1973 | Guillot et al. |
| 5,480,883 A * | 1/1996 | Spada et al. ............ 514/249 |
| 6,872,731 B1 * | 3/2005 | Crawforth et al. ....... 514/300 |

FOREIGN PATENT DOCUMENTS

| CH | 451 156 | 5/1968 |
| EP | 0 069 784 A1 | 5/1982 |
| EP | 0 069 784 B1 | 12/1987 |
| EP | 0 928 790 A1 | 7/1999 |
| FR | 7 428 M | 12/1969 |
| FR | 2 252 808 | 6/1975 |
| WO | WO 95 09852 A1 | 4/1995 |
| WO | WO 99 62890 | 12/1999 |
| WO | WO 00 02871 A1 | 1/2000 |
| WO | WO 00 26203 A1 | 5/2000 |
| WO | WO 01 17995 A1 | 3/2001 |
| WO | WO 02 45652 A2 | 6/2002 |
| WO | WO 03 000687 A1 | 1/2003 |
| WO | WO 03 015717 | 2/2003 |

OTHER PUBLICATIONS

STN result (accession No. 1955:35987).*
Spada et al., CAS Document No. 124:261073.*
Lawrence & Niu, Protein Kinase Inhibitors: the Tyrosine-Specific Protein Kinases Pharmacol. Ther. 77(2):81-114 (1998).*
Rossberg & Magun, Piezoelectricity of Ice, NATURWISSENSCHAFTEN 44:59 (1957).*
Gol'dfarb & Kondkova, Synthesis of carbazi-condensed systems form α-and α'-aminonicotines, Zhurnal Prikladnoi Khimi 15:151-63 (1942).*
Hu et al., Solubale Vascular Endothelial Growth Factor Receptor 1, and Not Receptor 2, Is an Independent Prognostic Factor in Acute Myeloid Leukemia and Myelodysplastic Syndromes, CANCER, 100(9):1884-91 (2004).*
Meshinchi et al., Activating Mutations of RTK/ras Signal Transduction Pathway in Pediatric Acute Myeloid Leukemia, Blood, 102(4):1474-1479 (2003).*
Schuch et al., In vivo Administration of Vascular Endothelial Growth Factor )VEGF) and its antagonist, soluble neuropilin-1, predicts a role of VEGF in the Progression of Acute Myeloid Leukemia in vivo, BLOOD, 100(13):4622-4628 (2002).*
J. Rak et al. Cancer Research, 55:4575-4580, 1995.
G. Gasparini and A.L. Harris, J. Clin. Oncol., 1995, 13:765-782.
M. Toi et al., Japan. J. Cancer Res., 1994, 85:1045-1049.
A.J. Dickinson et al., Br. J. Urol., 1994, 74:762-766.
L.M. Ellis et al., Surgery, 1996, 120(5):871-878.
J.K. Williams et al., Am. J. Surg., 1994, 168:373-380.
A. Amirkhosravi et al., Platelets, 10:285-292 (1999).
S.P. Gunningham, et al., Can. Research, 61: 3206-3211 (2001).
A. Giatromanolaki et al., J. Pathol. 2001; 194:101-108.
Michael Detmar, J. Dermatological Sci., 24 Suppl. 1, S78-S84 (2000).
Hasegawa et al., Skeletal Radiol., vol. 28, pp. 41-45, 1999.
Brockelsby et al., Laboratory Investigation 79:1101-1111 (Sep. 1999).
Paul et al., Nature Med 7:222-227 (2001).
Matsuyama et al., J. Neurol. Sci. 186:75-79 (2001).
van der Flier et al., J. Infectious Diseases. 183:149-153 (2001).
Stephen K. Smith, Trends in Endocrinology & Metabolism, vol. 12, No. 4, pp. 147-151, May/Jun. 2001.

(Continued)

Primary Examiner—Celia Chang
Assistant Examiner—R. James Balls
(74) Attorney, Agent, or Firm—Dianne Brown; Mark R. Daniel

(57) ABSTRACT

The present invention relates to imidazopyridine compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

7 Claims, No Drawings

OTHER PUBLICATIONS

Levis et al., Blood, vol. 98, No. 3, pp. 885-887 (2001).
Rajesh K. Jain, Nature Medicine, vol. 7. No. 9, pp. 987-989 (Sep. 2001).
Giulio Jori, Lasers Med. Sci., 1990; 5: 115-120.
Chuannong Zhou, J. Photochem. and Photobiol. 1989; 3:299-318.
Hendrich et al., Knee Surg Sports Traumatol Arthroscopy 5: 58-63 (1997).
Hall et al., Am J Hum Genet 61:785-789, 1997.
Li et al., Gene Therapy, 1998; 5:1105-13.
Fathallah-Shaykh et al., J Immunol 2000; 164:217-222.
Dougherty et al., J. Natl. Cancer Inst., 1998, 90(12): 889-905.
Van Bruggen et al., J. Clin. Invest,. 104:1613-1620 (1999).
Gerber et al., Nature Medicine, vol. 5, No. 6, pp. 623-628, 1999.
David A. Greenberg, Drug News Perspect 11(5):265-270 (1998).
Nakagawa et al., FEBS Let. 473:161-164 (2000).
Peter Traxler, Exp. Opin. Ther. Patents 8 (12) 1599-1625(1998).
Peter M. Traxler, Exp. Opin. Ther. Patents 7(6) 571-588 (1997).
Joseph V. Simone, Cecil Textbook of Medicine 20th Edition, vol. 1, pp. 1004-1010 (1996).
Lawrence et al., Pub Med Abstract, vol. 77(2), pp. 81-114 (1998).
Cuckler, et al., Nithiazide I. Chemical and Biological Studies, vol. 92, pp. 483-488 (1956).
Nagano, et al., Studies on Organic Sulfur Compounds, vol. 21, pp. 2408-2416 (1973).
Werbel, et al., Journal of Medicinal Chemistry, vol. 15, No. 9 pp. 955-963 (1972).
Micich, et al., Journal of the American Oil Chemists' Society, vol. 59, No. 10 pp. 448-452 (1982).
Wu, et al., Bio & Med Chem Letters, vol. 14, pp. 909-912 (2004).

* cited by examiner

TYROSINE KINASE INHIBITORS

PRIORITY CLAIM

This application is a §371 application of PCT/US03/13353 that was filed on Apr. 28, 2003, which claims priority from the U.S. Provisional Application No. 60/377,502, filed on May 2, 2002, now expired.

BACKGROUND OF THE INVENTION

The present invention relates to imidazopyridine compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates, as described in U.S. Pat. No. 6,245,759 B1 (hereby incorporated by reference).

Angiogenesis is characterized by excessive activity of vascular endothelial growth factor (VEGF) (as described in U.S. Pat. No. 6,245,759 B1). KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

SUMMARY OF THE INVENTION

The present invention relates to imidazopyridine compounds that are capable of inhibiting, modulating and/or regulating signal transduction of both receptor-type and non-receptor type tyrosine kinases.

DETAILED DESCRIPTION OF THE INVENTION

The compounds of this invention are useful in the inhibition of kinases and are illustrated by a compound of Formula I:

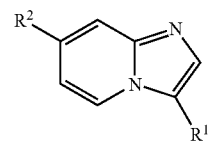

or a pharmaceutically acceptable salt or stereoisomer thereof, wherein
a is 0 or 1;
b is 0 or 1;
m is 0, 1, or 2;
$R^1$ is selected from:
  1) aryl,
  2) $C_3$–$C_5$ cycloalkyl;
  3) $C_2$–$C_3$ alkenyl;
  4) $C_2$–$C_3$ alkynyl and
  5) heteroaryl,
said aryl, cycloalkyl and heteroaryl is optionally substituted with one or more substituents selected from $R^3$;
$R^2$ is selected from:
  1) aryl,
  2) $C_3$–$C_8$ cycloalkyl and
  3) heterocyclyl,
said aryl, cycloalkyl and heterocyclyl is optionally substituted with one or more substituents selected from $R^4$;
$R^3$ is:
  1) $(C=O)_aO_bC_1$–$C_3$ alkyl,
  2) $CO_2H$,
  3) halo,
  4) CN,
  5) OH,
  6) $O_bC_1$–$C_3$ perfluoroalkyl,
  7) $O_a(C=O)_bNH_2$, 8) oxo,
9) CHO, or
10) (N=O)H$_2$;

R$^4$ is:
1) (C=O)$_a$O$_b$C$_1$–C$_{10}$ alkyl,
2) (C=O)$_a$O$_b$aryl,
3) C$_2$–C$_{10}$ alkenyl,
4) C$_2$–C$_{10}$ alkynyl,
5) (C=O)$_a$O$_b$ heterocyclyl,
6) CO$_2$H,
7) halo,
8) CN,
9) OH,
10) O$_b$C$_1$–C$_6$ perfluoroalkyl,
11) O$_a$(C=O)$_b$NR$^6$R$^7$,
12) oxo,
13) CHO,
14) (N=O)R$^6$R$^7$, or
15) (C=O)$_a$O$_b$C$_3$–C$_8$ cycloalkyl,
said alkyl, aryl, alkenyl, alkynyl, heterocyclyl, and cycloalkyl optionally substituted with one or more substituents selected from R$^5$;

R$^5$ is selected from:
1) (C=O)$_r$O$_s$(C$_1$–C$_{10}$)alkyl, wherein r and s are independently 0 or 1,
2) O$_r$(C$_1$–C$_3$)perfluoroalkyl, wherein r is 0 or 1,
3) (C$_0$–C$_6$)alkylene-S(O)$_m$R$^a$,
4) oxo,
5) OH,
6) halo,
7) CN,
8) (C$_2$–C$_{10}$)alkenyl,
9) (C$_2$–C$_{10}$)alkynyl,
10) (C$_3$–C$_6$)cycloalkyl,
11) (C$_0$–C$_6$)alkylene-aryl,
12) (C$_0$–C$_6$)alkylene-heterocyclyl,
13) (C$_0$–C$_6$)alkylene-N(R$^b$)$_2$,
14) C(O)R$^a$,
15) (C$_0$–C$_6$)alkylene-CO$_2$R$^a$,
16) C(O)H, and
17) (C$_0$–C$_6$)alkylene-CO$_2$H,
said alkyl, alkenyl, alkynyl, cycloalkyl, aryl, and heterocyclyl is optionally substituted with up to three substituents selected from R$^b$, OH, (C$_1$–C$_6$)alkoxy, halogen, CO$_2$H, CN, O(C=O)C$_1$–C$_6$ alkyl, oxo, and N(R$^b$)$_2$;

R$^6$ and R$^7$ are independently selected from:
1) H,
2) (C=O)O$_b$C$_1$–C$_{10}$ alkyl,
3) (C=O)O$_b$C$_3$–C$_8$ cycloalkyl,
4) (C=O)O$_b$aryl,
5) (C=O)O$_b$heterocyclyl,
6) C$_1$–C$_{10}$ alkyl,
7) aryl,
8) C$_2$–C$_{10}$ alkenyl,
9) C$_2$–C$_{10}$ alkynyl,
10) heterocyclyl,
11) C$_3$–C$_8$ cycloalkyl,
12) SO$_2$R$^a$, and
13) (C=O)NR$^b$$_2$,
said alkyl, cycloalkyl, aryl, heterocylyl, alkenyl, and alkynyl is optionally substituted with one or more substituents selected from R$^5$, or
R$^6$ and R$^7$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from R$^5$;

R$^a$ is (C$_1$–C$_6$)alkyl, (C$_3$–C$_6$)cycloalkyl, aryl, or heterocyclyl; and R$^b$ is H, (C$_1$–C$_6$)alkyl, aryl, heterocyclyl, (C$_3$–C$_6$)cycloalkyl, (C=O)OC$_1$–C$_6$ alkyl, (C=O)C$_1$–C$_6$ alkyl or S(O)$_2$R$^a$.

A second embodiment of the present invention is illustrated by a compound of Formula I, or a pharmaceutically acceptable salt or stereoisomer thereof, wherein
a is 0 or 1;
b is 0 or 1;
m is 0, 1, or 2;
R$^1$ is selected from: phenyl, thienyl, pyridyl, cyclopropyl and cyclobutyl;
said phenyl, thienyl and pyridyl is optionally substituted with one or two substituents selected from R$^3$;
R$^2$ is selected from:
1) aryl,
2) C$^3$–C$^8$ cycloalkyl and
3) heterocyclyl,
said aryl, cycloalkyl and heterocyclyl is optionally substituted with one or more substituents selected from R$^4$;

R$^3$ is:
1) (C=O)$_a$O$_b$C$_1$–C$_3$ alkyl,
2) CO$_2$H,
3) halo,
4) CN,
5) OH,
6) O$_b$C$_1$–C$_3$ perfluoroalkyl,
7) O$_a$(C=O)$_b$NH$_2$,
8) oxo,
9) CHO, or
10) (N=O)H$_2$;

R$^4$ is:
1) (C=O)$_a$O$_b$C$_1$–C$_{10}$ alkyl,
2) (C=O)$_a$O$_b$aryl,
3) C$_2$–C$_{10}$ alkenyl,
4) C$_2$–C$_{10}$ alkynyl,
5) (C=O)$_a$O$_b$ heterocyclyl,
6) CO$_2$H,
7) halo,
8) CN,
9) OH,
10) O$_b$C$_1$–C$_6$ perfluoroalkyl,
11) O$_a$(C=O)$_b$NR$^6$R$^7$,
12) oxo,
13) CHO,
14) (N=O)6R$^7$, or
15) (C=O)$_a$O$_b$C$_3$–C$_8$ cycloalkyl,
said alkyl, aryl, alkenyl, alkynyl, heterocyclyl, and cycloalkyl optionally substituted with one or more substituents selected from R$^5$;

R$^5$ is selected from:
1) (C=O)$_r$O$_s$(C$_1$–C$_{10}$)alkyl, wherein r and s are independently 0 or 1,
2) O$_r$(C$_1$–C$_3$)perfluoroalkyl, wherein r is 0 or 1,
3) (C$_0$–C$_6$)alkylene-S(O)$_m$R$^a$,
4) oxo,
5) OH,
6) halo,
7) CN,
8) (C$_2$–C$_{10}$)alkenyl,
9) (C$_2$–C$_{10}$)alkynyl,
10) (C$_3$–C$_6$)cycloalkyl, 11) $(C_0–C_6)$alkylene-aryl,
12) $(C_0–C_6)$alkylene-heterocyclyl,
13) $(C_0–C_6)$alkylene-N$(R^b)_2$,
14) C(O)$R^a$,
15) $(C_0–C_6)$alkylene-CO$_2R^a$,
16) C(O)H, and
17) $(C_0–C_6)$alkylene-CO$_2$H, said alkyl, alkenyl, alkynyl, cycloalkyl, aryl, and heterocyclyl is optionally substituted with up to three substituents selected from $R^b$, OH, $(C_1–C_6)$alkoxy, halogen, CO$_2$H, CN, O(C=O)C$_1$–C$_6$ alkyl, oxo, and N$(R^b)_2$;

$R^6$ and $R^7$ are independently selected from:
1) H,
2) (C=O)O$_b$C$_1$–C$_{10}$ alkyl,
3) (C=O)O$_b$C$_3$–C$_8$ cycloalkyl,
4) (C=O)O$_b$aryl,
5) (C=O)O$_b$heterocyclyl,
6) C$_1$–C$_{10}$ alkyl,
7) aryl,
8) C$_2$–C$_{10}$ alkenyl,
9) C$_2$–C$_{10}$ alkynyl,
10) heterocyclyl,
11) C$_3$–C$_8$ cycloalkyl,
12) SO$_2R^a$, and
13) (C=O)NR$^b{}_2$, said alkyl, cycloalkyl, aryl, heterocylyl, alkenyl, and alkynyl is optionally substituted with one or more substituents selected from $R^5$, or $R^6$ and $R^7$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^5$;

$R^a$ is $(C_1–C_6)$alkyl, $(C_3–C_6)$cycloalkyl, aryl, or heterocyclyl; and $R^b$ is H, $(C_1–C_6)$alkyl, aryl, heterocyclyl, $(C_3–C_6)$cycloalkyl, (C=O)OC$_1$–C$_6$ alkyl, (C=O)C$_1$–C$_6$ alkyl or S(O)$_2R^a$.

A third embodiment of the invention is a compound of Formula I, wherein $R^1$ is selected from phenyl and pyridyl, optionally substituted with one or more substituents selected from $R^3$; and $R^2$ is selected from phenyl, pyridyl and 1,2-dihydropyridinyl, optionally substituted with one to three substituents selected from $R^4$.

A preferred embodiment is a compound selected from
3,7-diphenylimidazo[1,2-a]pyridine
7-phenyl-3-pyridin-4-ylimidazo[1,2-a]pyridine
7-phenyl-3-pyridin-3-ylimidazo[1,2-a]pyridine
[4-(3-phenylimidazo[1,2-a]pyridin-7-yl)phenyl]methanol
7-(4-{[4-(methylsulfonyl)piperazin-1-yl]methyl}phenyl)-3-phenylimidazo[1,2-a]pyridine
4-methyl-1-[4-(3-phenylimidazo[1,2-a]pyridin-7-yl)benzyl]-1,4-diazepan-5-one
7-{4-[(4-acetylpiperazin-1-yl)methyl]phenyl}-3-phenylimidazo[1,2-a]pyridine
N-methyl-4-[4-(3-phenylimidazo[1,2-a]pyridin-7-yl)benzyl]piperazine-1-carboxamide
4-[4-(3-phenylimidazo[1,2-a]pyridin-7-yl)benzyl]piperazine-1-carboxamide
1-[4-(3-phenylimidazo[1,2-a]pyridin-7-yl)benzyl]-1,4-diazepan-5-one
7-(4-{[4-(methylsulfonyl)piperidin-1-yl]methyl}phenyl)-3-phenylimidazo[1,2-a]pyridine
3-phenyl-7-(4-pyridyl)imidazo[1,2-a]pyridine
7-(1-oxy-pyridin-4-yl)-3-phenyl-imidazo[1,2-a]pyridine
4-(3-phenyl-imidazo[1,2-a]pyridin-7-yl)-1H-pyridin-2-one or a pharmaceutically acceptable salt thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $R^6$, $R^7$, $R^b$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, C$_1$–C$_{10}$, as in "C$_1$–C$_{10}$ alkyl" is defined to include groups having 1, 2, 3, 4, 5, 6, 7, 8, 9 or 10 carbons in a linear or branched arrangement. For example, "C$_1$–C$_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "C$_2$–C$_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, 1H-pyridin-2-one, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

Preferably, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

The alkyl, alkenyl, alkynyl, cycloalkyl, aryl, heteroaryl and heterocyclyl substituents may be unsubstituted or unsubstituted, unless specifically defined otherwise. For example, a ($C_1$–$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)$CH_2$CH(OH)$CH_3$, —(C=O)OH, —$CH_2$(OH)$CH_2$CH(O), and so on.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

In certain instances, $R^6$ and $R^7$ are defined such that they can be taken together with the nitrogen to which they are attached to form a monocyclic or bicyclic heterocycle with 5–7 members in each ring and optionally containing, in addition to the nitrogen, one or two additional heteroatoms selected from N, O and S, said heterocycle optionally substituted with one or more substituents selected from $R^5$. Examples of the heterocycles that can thus be formed include, but are not limited to the following, keeping in mind that the heterocycle is optionally substituted with one or more substituents chosen from $R^5$:

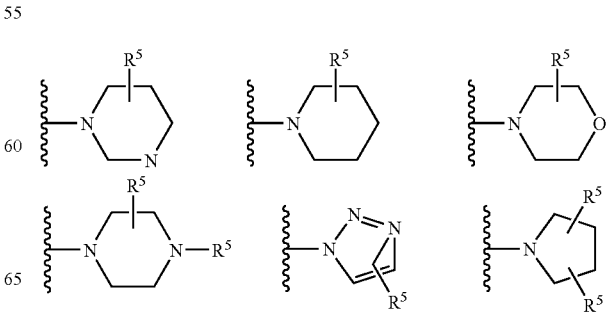

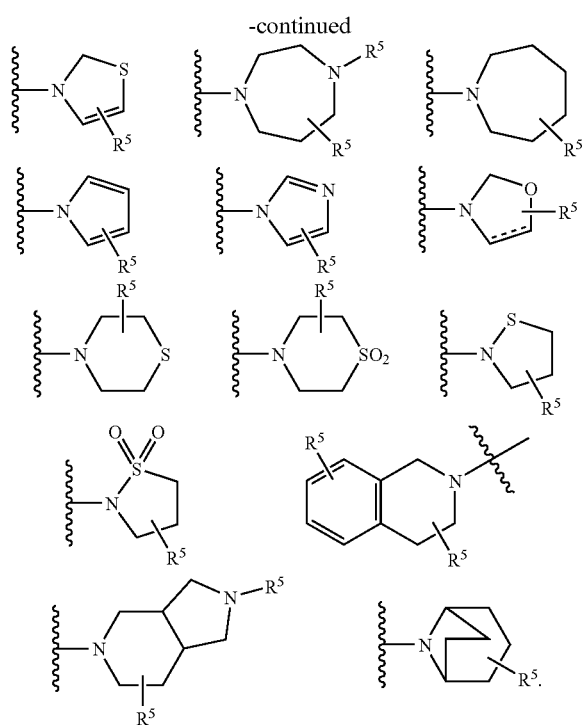

Preferably $R^1$ is is selected from phenyl and pyridyl, optionally substituted with one or two $R^3$.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

Schemes

As shown in Scheme A, 4-iodopyriidine-2-carboxylic acid can be converted to the corresponding protected amine A-1. Reaction of intermediate A-1 with a suitable boronic acid provides the substituted intermediate A-2, which can be deprotected and treated with bromoacetaldehyde to provide the imidazopyridine intermediate A-4. Iodination of the ring, followed by reaction with a second suitable boronic acid reagent provides the compound of the instant invention A-6.

Scheme B illustrates how functional groups on the $R^2$ substituent, such as the aldehyde moiety shown, can be modified to allow incorporation of other substituents.

Preparation of a compound of the instant invention having a $R^2$ which is pyridyl is illustrated in Scheme C. The instant compound C-4 may itself be oxidized to form the pyridyl N-oxide analog C-5. Reaction of instant compound C-5 with acetic anhydride provides the pyridinone C-6. Scheme D illustrates the subsequent substitution on the pyridinone nitrogen.

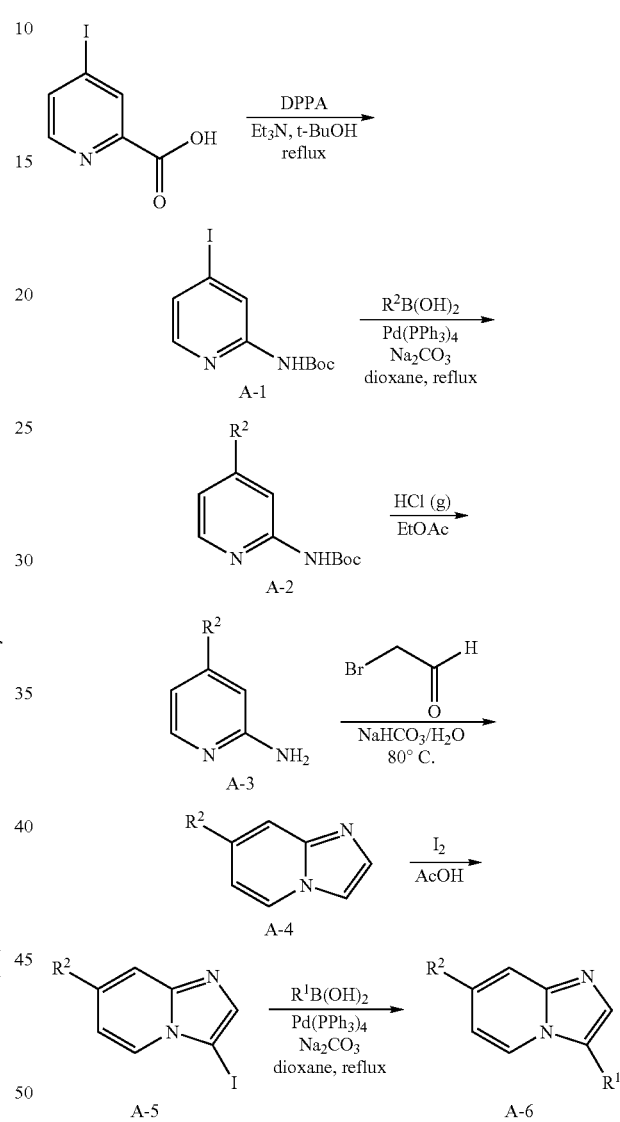

SCHEME B

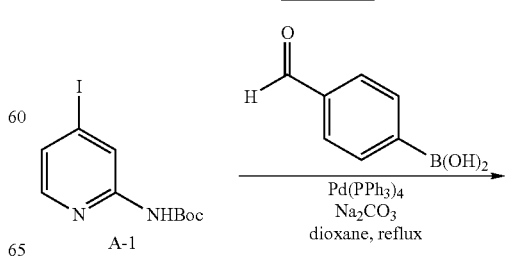

-continued
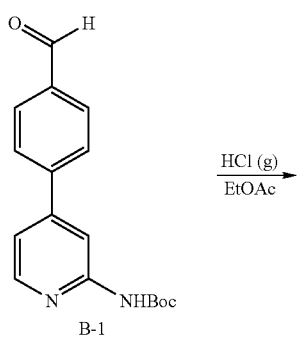
B-1
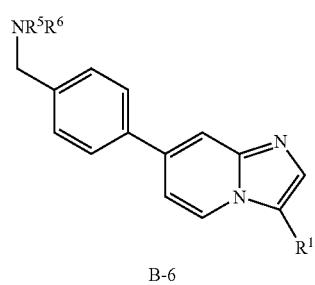
B-6
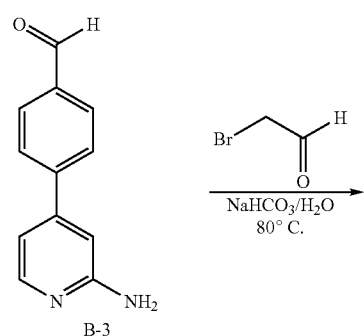
B-3
SCHEME C
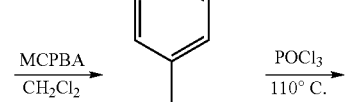
C-1
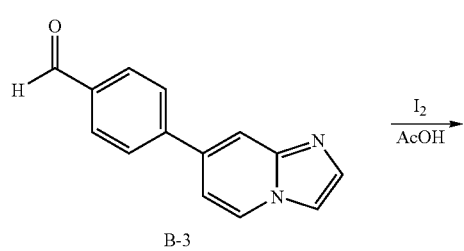
B-3
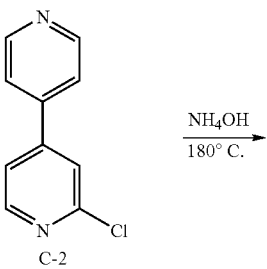
C-2
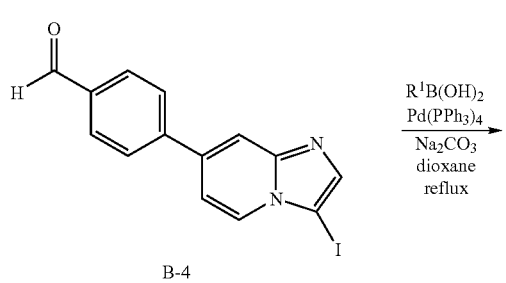
B-4
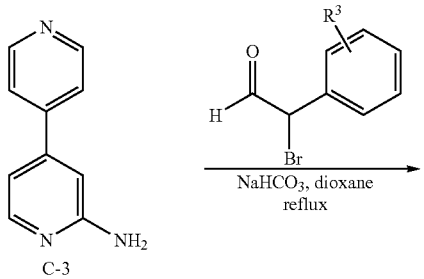
C-3
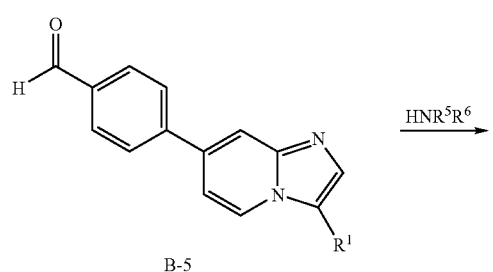
B-5
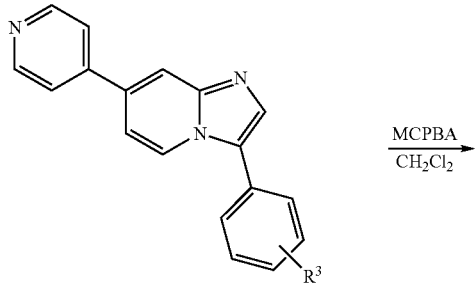
C-4

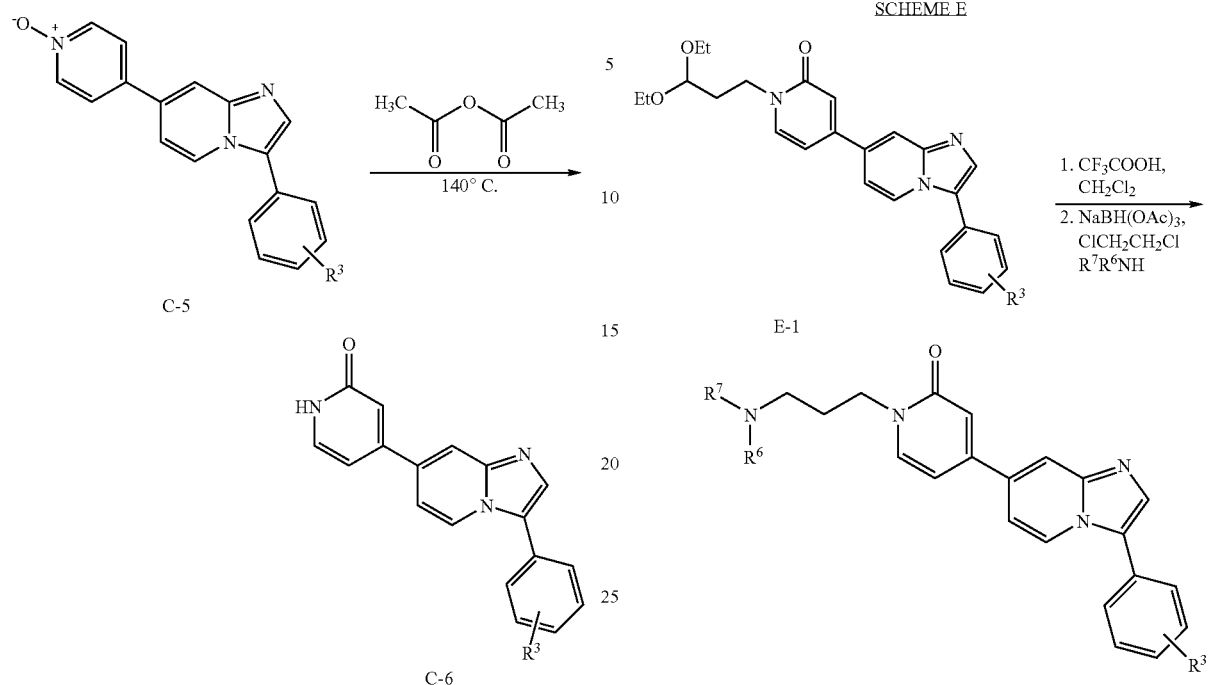
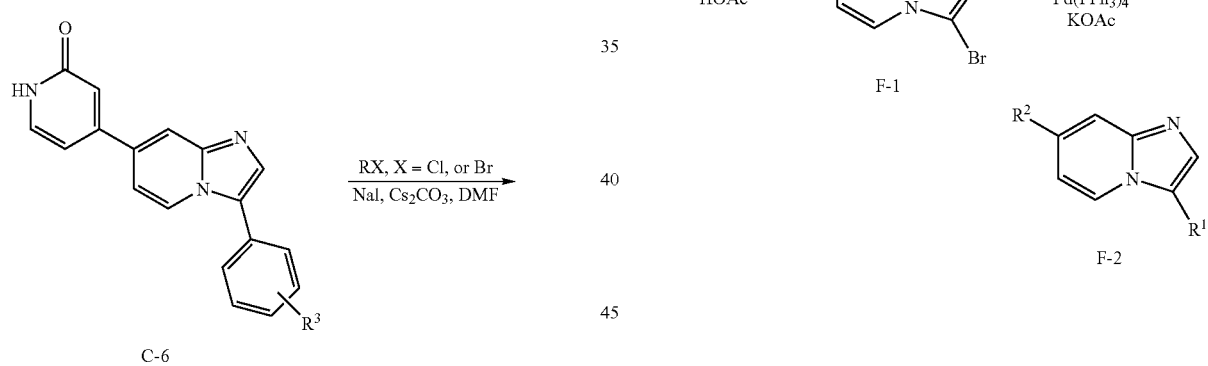
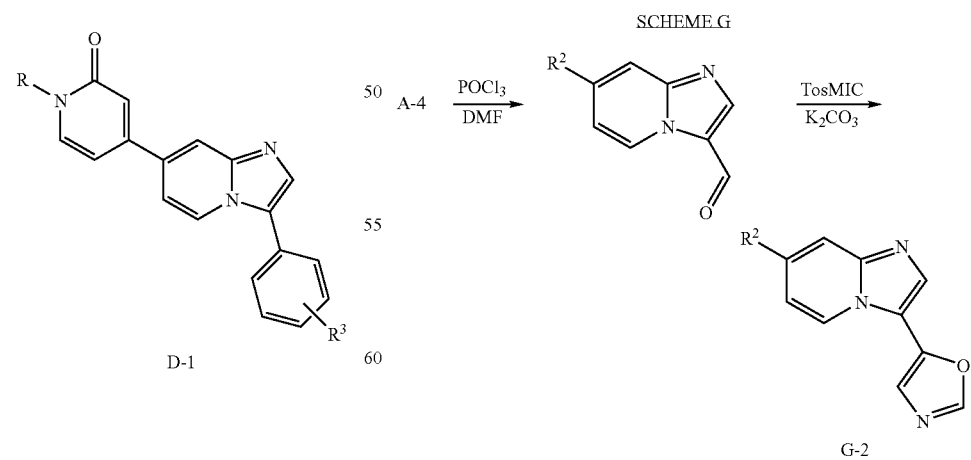

Utilities

The compounds of the present invention are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like). In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a claimed compound. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. A further preferred group of cancers for treatment with the present compounds is a cancer selected from lung cancer, prostate cancer, breast cancer and colorectal cancer. The utility of angiogenesis inhibitors in the treatment of cancer is known in the literature, see J. Rak et al. *Cancer Research,* 55:4575–4580, 1995, for example. The role of angiogenesis in cancer has been shown in numerous types of cancer and tissues: breast carcinoma (G. Gasparini and A. L. harris, *J. Clin. Oncol.,* 1995, 13:765–782; M. Toi et al., *Japan. J. Cancer Res.,* 1994, 85:1045–1049); bladder carcinomas (A. J. Dickinson et al., *Br. J. Urol.,* 1994, 74:762–766); colon carcinomas (L. M. Ellis et al., *Surgery,* 1996, 120(5):871–878); and oral cavity tumors (J. K. Williams et al., *Am. J. Surg.,* 1994, 168:373–380).

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets,* 10:285–292 (1999)). In fact, angiogenesis is essential for tumor growth and metastasis. (S. P. gunningham, et al., *Can. Research,* 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108.) For the role of VEGF in skin angiogenesis, see Michael Detmar, *J. Dermatological Sci.,* 24 Suppl. 1, S78–S84 (2000).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.,* 28, pp. 41–45, 1999; Gerber et al., *Nature Medicine,* Vol. 5, No. 6, pp. 623–628, June 1999.) And since VEGF directly promotes osteoclastic bone resorption through KDR/Flk-1 expressed in mature osteoclasts (FEBS Let. 473:161–164 (2000); *Endocrinology,* 141:1667 (2000)), the instant compounds are also useful to treat and prevent conditions related to bone resorption, such as osteoporosis and Paget's disease.

A method of treating or preventing preeclampsia is also within the scope of the present invention, which comprises administering a therapeutically effective amount of a compound of Formula I. Studies have shown that the action of VEGF on the Flt-1 receptor is pivotal in the pathogenesis of preeclampsia. (*Laboratory Investigation* 79:1101–1111 (September 1999).) Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of the present invention. The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

The instant compounds can also be used to prevent or treat tissue damage during bacterial meningitis, such as tuberculous meningitis. (Matsuyama et al., *J. Neurol. Sci.* 186: 75–79 (2001)). The instant invention therefore encompasses a method of treating or preventing tissue damage due to bacterial meningitis which comprises administering a therapeutically effective amount of a claimed compound. Studies have shown that VEGF is secreted by inflammatory cells during bacterial meningitis and that VEGF contributes to blood-brain barrier disruption. (van der Flier et al., *J. Infectious Diseases,* 183:149–153 (2001)). The claimed compounds can inhibit VEGF-induced vascular permeability and therefore serve to prevent or treat blood-brain barrier disruption associated with bacterial meningitis.

The present invention further encompasses a method to treat or prevent endometriosis comprised of administering a therapeutically effective amount of a claimed compound. An increase in VEGF expression and angiogenesis is associated with the progression of endometriosis (Stephen K. Smith, *Trends in Endocrinology & Metabolism,* Vol. 12, No. 4, May/June 2001). Inhibition of VEGF by the current compounds would therefore inhibit angiogenesis and treat endometriosis.

A further embodiment of the present invention is a method of treating acute myeloid leukemia (AML) which comprises administering a therapeutically effective amount of a claimed compound. Activation of FLT3 on leukemic cells by FLT3 ligand leads to receptor dimerization and signal transduction in pathways that promote cell growth and inhibit apoptosis (*Blood,* Vol. 98, No. 3, pp. 885–887 (2001)). The present compounds are therefore useful to treat AML via inhibition of the tyrosine kinase domain of Flt-3.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and cornstarch, and lubricating agents, such as magnesium stearate, are commonly added. For oral administration in capsule form, useful diluents include lactose and dried cornstarch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186). The use of angiogenesis inhibitors with other chemotherapeutic agents is especially desirable since the normalization of tumor vasculature improves the delivery of the other therapeutic agents. (Nature Medicine, Vol. 7. No. 9, pp. 987–989 (September 2001)).

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate. For an example of a previously reported combination of an androgen receptor modulator (a non-steroidal anti-androgen, in this case) and a tyrosine kinase inhibitor, see WO 0176586, published on 18 Oct. 2001.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23–7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7] indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one,2,3-(methylenedioxy)-5-methyl-7-hydroxy-8-methoxybenzo[c]-phenanthridinium,6,9-bis[(2-aminoethyl)amino]benzo[g]isoguinoline-5,10-dione,5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

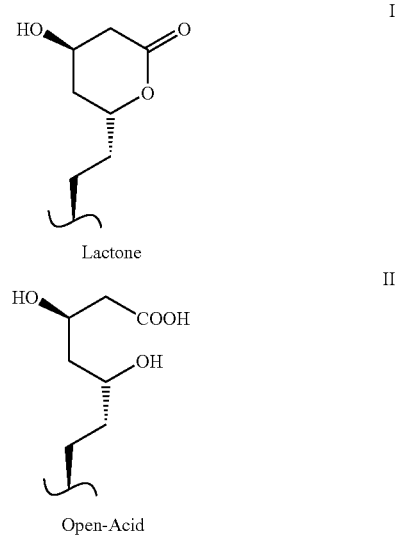

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18, 19-dihydro-19-oxo-5H,17H-6,10:12,16-dimetheno-1H-imidazo[4,3-c][1,11,4]dioxaazacyclo-nonadecene-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp. 963–968 (October 1999); Kim et al., Nature, 362, 841–844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679–692 (2000)). Examples of such agents that modulate or inhibit the coagulation and fibrinolysis pathways include, but are not limited to, heparin (see *Thromb. Haemost.* 80:10–23 (1998)), low molecular weight heparins and carboxypeptidase U inhibitors (also known as inhibitors of active thrombin activatable fibrinolysis inhibitor [TAFIa]) (see *Thrombosis Res.* 101: 329–354 (2001)). TAFIa inhibitors have been described in U.S. Ser. Nos. 60/310,927 (filed Aug. 8, 2001) and 60/349, 925 (filed Jan. 18, 2002).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

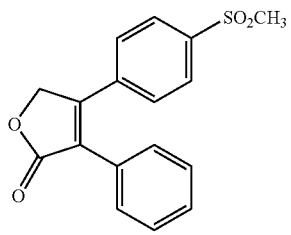

5-chloro-3-(4-methylsulfonyl)phenyl-2-(2-methyl-5-pyridinyl)pyridine;

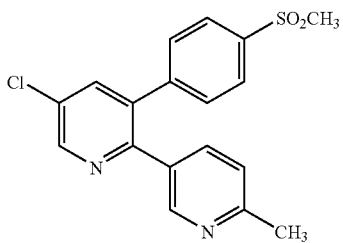

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

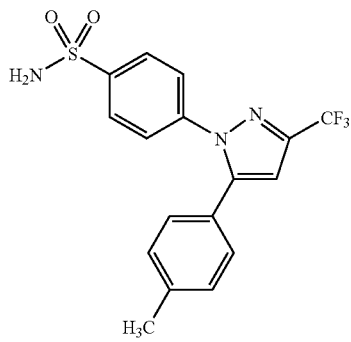

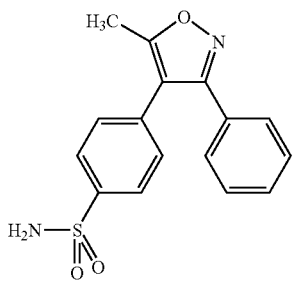

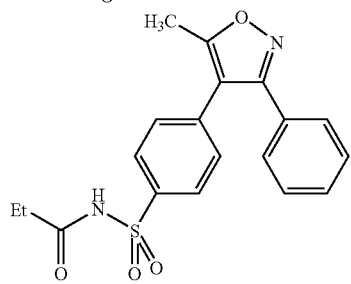

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxy]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH-268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

Combinations with compounds other than anti-cancer compounds are also encompassed to treat conditions other than cancer. For example, combinations of the instantly claimed compounds with PPAR-γ (i.e., PPAR-gamma) agonists are useful in the treatment of diabetic retinopathy. PPAR-γ is the nuclear peroxisome proliferator-activated receptor γ. The expression of PPAR-γ on endothelial cells and its involvement in angiogenesis in corneal and choroidal experimental systems has been reported in the literature (see *J. Cardiovasc. Pharmacol.* 1998; 31:909–913; *J. Biol. Chem.* 1999;274:9116–9121; *Invest. Ophthalmol Vis. Sci.* 2000; 41:2309–2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709–717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697). Thus, a method of treating or preventing diabetic retinopathy which comprises administering a therapeutically effective amount of a claimed compound in combination with a PPAR-γ agonist is also within the scope of the present invention.

Another aspect of the invention is illustrated by a composition comprising a therapeutically effective amount of the disclosed tyrosine kinase inhibitors and a steroidal anti-inflammatory. Steroidal anti-inflammatories include, but are not limited to, corticosteroids, mineralocorticoids, dexamethasone, prednisone, prednisolone, methylpred, and betamethasone. This combination is particularly useful in ophthalmic formulations that may, in some cases, be associated with irritation of the ocular tissues.

A particularly useful combination for the treatment of diseases wherein aberrant angiogensis is present involves administering a therapeutically effective amount of the instantly disclosed tyrosine-kinase inhibiting compounds in combination with photodynamic therapy and a photosensitive drug such as verteoporfin (BPD-MA) (Carruth, Clinical Applications of Photodynamic Therapy, Int. J. Clin. Pract. 1998; 52(1):39–42). Such diseases include, but are not limited to, age-related macular degeneration (Bressler, Treatment of Age-Related Macular Degeneration with Photodynamic Therapy Investigation Using Verteoporfin, Invest. Ophthalmol. Vis. Sci. 1998; 39 S242), cancer, especially melanoma and non-melanoma skin cancer, including basal cell and squamous cell carcinomas, (Hassan and Parrish, Photodynamic Therpay in Cancer, Cancer Med 1997; Dougherty et al., Photodynamic Therapy for the Treatment of Cancer: Current Status and Advances in Photodynamic Therapy of Neoplastic Disease. Kessel (Ed.), CRC Press, 1989; 1–19); Dougherty et al., Photodynamic Therpay, J. Natl. Cancer Inst., 1998, 90(12): 889–905; Jori, Factors Controlling the Selectivity and Efficiency of Tumour Damage in Photodynamic Therapy, Laser Med. Sci. 1990; 5: 115–120; Zhou, Mechanism of Tumour Necrosis Induced by Photodynamic Therapy, J. Photochem. Photobiol. 1989; 3: 299–318), psoriasis (Bissonnette et al., Photodynamic Therapy of Psoriasis and Psoriatic Arthritis with BPD verteporfin. 7$^{th}$ Biennial Congress, International Photodynamic Association, Nantes, France 1998:73), and rheumatoid arthritis (Hendrich et al., Photodynamic Therapy for Rheumatoid Arthritis. Lasermedizin 11: 73–77 (1995); Hendrich et al. Photodynamic Laser Therapy for Rheumatoid Arthritis: Cell Culture Studies and Animal Experiments, Knee Surg Sports Traumatol Arthroscopy 5: 58–63 (1997).

Another embodiment of the instant invention is the use of the presently disclosed compounds in combination with gene therapy for the treatment of cancer. For an overview of genetic strategies to treating cancer see Hall et al (Am J Hum Genet 61:785–789, 1997) and Kufe et al (Cancer Medicine, 5th Ed, pp 876–889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998;5(8):1105–13), and interferon gamma (J Immunol 2000;164:217–222).

VEGF receptor tyrosine kinase have been reported to cause a sustained increase in blood pressure in rats when administered more than once, particularly when administered chronically. It is desirable, however, to produce an antiangiogenic effect without causing hypertension. This can be achieved by treating a disease state associated with angiogenesis with a therapeutically effective amount of a combination of an anti-angiogenic agent, such as those presently disclosed, and an anti-hypertensive agent (see WO 01/74360, hereby incorporated by reference). The present invention therefore encompasses a pharmaceutical composition comprising a therapeutically effective amount of a combination of a compound of Formula I and an anti-hypertensive compound.

An anti-hypertensive is any agent which lowers blood pressure. There are numerous categories of anti-hypertensive agents including calcium channel blockers, angiotensin converting enzyme inhibitors (ACE inhibitors), angiotensin II receptor antagonists (A-II antagonists), diuretics, beta-adrenergic receptor blockers (β-blockers), vasodilators, alpha-adrenergic receptor blockers (α-blockers), selective neutral endopeptidase (NEP) inhibitors and dual ACE-NEP inhibitors. Any anti-hypertensive agent may be used in accordance with this invention and examples from each class are given below.

Calcium channel blockers which are within the scope of this invention include, but are not limited to: amlodipine (U.S. Pat. No. 4,572,909); bepridil (U.S. Pat. No. 3,962,238 or U.S. Pat. Reissue No. 30,577); clentiazem (U.S. Pat. No. 4,567,175); diltiazem (U.S. Pat. No. 3,562,257); fendiline (U.S. Pat. No. 3,262,977); gallopamil (U.S. Pat. No. 3,261,859); mibefradil (U.S. Pat. No. 4,808,605); prenylamine (U.S. Pat. No. 3,152,173); semotiadil (U.S. Pat. No. 4,786,635); terodiline (U.S. Pat. No. 3,371,014); verapamil (U.S. Pat. No. 3,261,859); aranidipine (U.S. Pat. No. 4,446,325); bamidipine (U.S. Pat. No. 4,220,649); benidipine (European Patent Application Publication No. 106,275); cilnidipine (U.S. Pat. No. 4,672,068); efonidipine (U.S. Pat. No. 4,885,284); elgodipine (U.S. Pat. No. 4,952,592); felodipine (U.S. Pat. No. 4,264,611); isradipine (U.S. Pat. No. 4,466,972); lacidipine (U.S. Pat. No. 4,801,599); lercanidipine (U.S. Pat. No. 4,705,797); manidipine (U.S. Pat. No. 4,892,875); nicardipine (U.S. Pat. No. 3,985,758); nifedipine (U.S. Pat. No. 3,485,847); nilvadipine (U.S. Pat. No. 4,338,322); nimodipine (U.S. Pat. No. 3,799,934); nisoldipine (U.S. Pat. No. 4,154,839); nitrendipine (U.S. Pat. No. 3,799,934); cinnarizine (U.S. Pat. No. 2,882,271); flunarizine (U.S. Pat. No. 3,773,939); lidoflazine (U.S. Pat. No. 3,267,104); lomerizine (U.S. Pat. No. 4,663,325); bencyclane (Hungarian Patent No. 151,865); etafenone (German Patent No. 1,265,758); and perhexiline (British Patent No. 1,025,578). The disclosures of all such patents and patent applications are incorporated herein by reference.

Angiotensin Converting Enzyme Inhibitors (ACE-Inhibitors) which are within the scope of this invention include, but are not limited to: alacepril (U.S. Pat. No. 4,248,883); benazepril (U.S. Pat. No. 4,410,520); captopril (U.S. Pat. Nos. 4,046,889 and 4,105,776); ceronapril (U.S. Pat. No. 4,452,790); delapril. (U.S. Pat. No. 4,385,051); enalapril (U.S. Pat. No. 4,374,829); fosinopril (U.S. Pat. No. 4,337,201); imidapril (U.S. Pat. No. 4,508,727); lisinopril (U.S. Pat. No. 4,555,502); moveltipril (Belgium Patent No. 893,553); perindopril (U.S. Pat. No. 4,508,729); quinapril (U.S. Pat. No. 4,344,949); ramipril (U.S. Pat. No. 4,587,258); spirapril (U.S. Pat. No. 4,470,972); temocapril (U.S. Pat. No. 4,699,905); and trandolapril (U.S. Pat. No. 4,933,361). The disclosures of all such patents are incorporated herein by reference.

Angiotensin-II receptor antagonists (A-II antagonists) which are within the scope of this invention include, but are not limited to: candesartan (U.S. Pat. No. 5,196,444); eprosartan (U.S. Pat. No. 5,185,351); irbesartan (U.S. Pat. No. 5,270,317); losartan (U.S. Pat. No. 5,138,069); and valsartan (U.S. Pat. No. 5,399,578. The disclosures of all such U.S. patents are incorporated herein by reference.

β-Blockers which are within the scope of this invention include, but are not limited to: acebutolol (U.S. Pat. No. 3,857,952); alprenolol (Netherlands Patent Application No. 6,605,692); amosulalol (U.S. Pat. No. 4,217,305); arotinolol (U.S. Pat. No. 3,932,400); atenolol (U.S. Pat. Nos. 3,663,607 and 3,836,671); befunolol (U.S. Pat. No. 3,853,923); betaxolol (U.S. Pat. No. 4,252,984); bevantolol (U.S. Pat. No. 3,857,891); bisoprolol (U.S. Pat. No. 4,258,062); bopindolol (U.S. Pat. No. 4,340,541); bucumolol (U.S. Pat. No. 3,663,570); bufetolol (U.S. Pat. No. 3,723,476); bufuralol (U.S. Pat. No. 3,929,836); bunitrolol (U.S. Pat. No. 3,541,130); bupranolol (U.S. Pat. No. 3,309,406); butidrine hydrochloride (French Patent No. 1,390,056); butofilolol (U.S. Pat. No. 4,302,601); carazolol (German Patent No. 2,240,599); carteolol (U.S. Pat. No. 3,910,924); carvedilol (U.S. Pat. No. 4,503,067); celiprolol (U.S. Pat. No. 4,034,009); cetamolol (U.S. Pat. No. 4,059,622); cloranolol (German Patent No. 2,213,044); dilevalol (Clifton et al., Journal of Medicinal Chemistry, 1982, 25, 670); epanolol (U.S. Pat. No. 4,167,581); indenolol (U.S. Pat. No. 4,045,482); labetalol (U.S. Pat. No. 4,012,444); levobunolol (U.S. Pat. No. 4,463,176); mepindolol (Seeman et al, Helv. Chim. Acta, 1971, 54, 2411); metipranolol (Czechoslovakian Patent Application No. 128,471); metoprolol (U.S. Pat. No. 3,873,600); moprolol (U.S. Pat. No. 3,501,769); nadolol (U.S. Pat. No. 3,935,267); nadoxolol (U.S. Pat. No. 3,819,702); nebivalol (U.S. Pat. No. 4,654,362); nipradilol (U.S. Pat. No. 4,394,382); oxprenolol (British Patent No. 1,077,603); penbutolol (U.S. Pat. No. 3,551,493); pindolol (Swiss Patents Nos. 469,002 and 472,404); practolol (U.S. Pat. No. 3,408,387); pronethalol (British Patent No. 909,357); propranolol (U.S. Pat. Nos. 3,337,628 and 3,520,919); sotalol (Uloth et al., Journal of Medicinal Chemistry, 1966, 9, 88); sulfinalol (German Patent No. 2,728,641); talinolol (U.S. Pat. Nos. 3,935,259 and 4,038,313); tertatolol (U.S. Pat. No. 3,960,891); tilisolol (U.S. Pat. No. 4,129,565); timolol (U.S. Pat. No. 3,655,663); toliprolol (U.S. Pat. No. 3,432,545); and xibenolol (U.S. Pat. No. 4,018,824). The disclosures of all such patents, patent applications and references are incorporated herein by reference.

α-Blockers which are within the scope of this invention include, but are not limited to: amosulalol (U.S. Pat. No. 4,217,305); arotinolol; dapiprazole (U.S. Pat. No. 4,252,721); doxazosin (U.S. Pat. No. 4,188,390); fenspiride (U.S. Pat. No. 3,399,192); indoramin (U.S. Pat. No. 3,527,761); labetolol; naftopidil (U.S. Pat. No. 3,997,666); nicergoline (U.S. Pat. No. 3,228,943); prazosin (U.S. Pat. No. 3,511,836); tainsulosin (U.S. Pat. No. 4,703,063); tolazoline (U.S. Pat. No. 2,161,93 8); trimazosin (U.S. Pat. No. 3,669,968);

and yohimbine. The disclosures of all such U.S. patents are incorporated herein by reference.

The term "vasodilator" as used herein is meant to include cerebral vasodilators, coronary vasodilators and peripheral vasodilators. Cerebral vasodilators within the scope of this invention include, but are not limited to: bencyclane; cinnarizine; citicoline; cyclandelate (U.S. Pat. No. 3,663,597); ciclonicate (German Patent No. 1,910,481); diisopropylamine dichloroacetate (British Patent No. 862,248); eburnamonine (Hermann et al., Journal of the American Chemical Society, 1979, 101, 1540); fasudil (U.S. Pat. No. 4,678,783); fenoxedil (U.S. Pat. No. 3,818,021); flunarizine (U.S. Pat. No. 3,773,939); ibudilast (U.S. Pat. No. 3,850,941); ifenprodil (U.S. Pat. No. 3,509,164); lomerizine (U.S. Pat. No. 4,663,325); nafronyl (U.S. Pat. No. 3,334,096); nicametate (Blicke et al., Journal of the American Chemical Society, 1942, 64, 1722); nicergoline; nimodipine (U.S. Pat. No. 3,799,934); papaverine (Goldberg, Chem. Prod. Chem. News, 1954, 17, 37 1; pentifylline (German Patent No. 860,217); tinofedrine (U.S. Pat. No. 3,767,675); vincamine (U.S. Pat. No. 3,770,724); vinpocetine (U.S. Pat. No. 4,035,750); and viquidil (U.S. Pat. No. 2,500,444). The disclosures of all such patents and references are incorporated herein by reference. Coronary vasodilators. within the scope of this invention include, but are not limited to: amotriphene (U.S. Pat. No. 3,010,965); bendazol (Feitelson, et al., J. Chem. Soc. 1958, 2426); benfurodil hemisuccinate (U.S. Pat. No. 3,355,463); benziodarone (U.S. Pat. No. 3,012,042); chloracizine (British Patent No. 740,932) chromonar (U.S. Pat. No. 3,282,93 8); clobenfural (British Patent No. 1,160,925); clonitrate; cloricromen (U.S. Pat. No. 4,452,811); dilazep (U.S. Pat. No. 3,532,685); dipyridamole (British Patent No. 807,826); droprenilamine (German Patent No. 2,521,113); efloxate (British Patents Nos. 803,372 and 824,547); erythrityl tetranitrate; etafenone (German Patent No. 1,265,758); fendiline (U.S. Pat. No. 3,262,977); floredil (German Patent No. 2,020,464); ganglefene (U.S.S.R. Patent No. 115,905); hexestrol bis(P-diethylaminoethyl)ether (Lowe et al., J. Chem. Soc. 1951, 3286); hexobendine (U.S. Pat. No. 3,267,103); itramin tosylate (Swedish Patent No. 168,308); khellin (Baxter et al., Journal of the Chemical Society, 1949, S 30); lidoflazine (U.S. Pat. No. 3,267,104); mannitol hexanitrate; medibazine (U.S. Pat. No. 3,119,826); nitroglycerin; pentaerythritol tetranitrate; pentrinitrol (German Patent No. 638,422-3); perhexiline; pimefylline (U.S. Pat. No. 3,350,400); prenylamine (U.S. Patent No. 3,152,173); propatyl nitrate (French Patent No. 1,103,113); trapidil (East German Patent No. 5 5,956); tricromyl (U.S. Pat. No. 2,769,015); trimetazidine (U.S. Pat. No. 3,262,852); trolnitrate phosphate; visnadine (U.S. Pat. Nos. 2,816,118 and 2,980,699. The disclosures of all such patents and references are incorporated herein by reference. Peripheral vasodilators within the scope of this invention include, but are not limited to: aluminium nicotinate (U.S. Pat. No. 2,970,082); bamethan (Corrigan et al., Journal of the American Chemical Society, 1945, 67, 1894); bencyclane; betahistine (Walter et al, Journal of the American Chemical Society, 1941, 63); bradykinin; brovincamine (U.S. Pat. No. 4,146,643); bufeniode (U.S. Pat. No. 3,542,870); buflomedil (U.S. Pat. No. 3,895,030); butalamine (U.S. Pat. No. 3,338,899); cetiedil (French Patent No. 1,460,571); ciclonicate (German Patent No. 1,910,481); cinepazide (Beiguim Patent No. 730,345); cinnarizine; cyclandelate; diisopropylamine dichloroacetate; eledoisin (British Patent No. 984,810); fenoxedil; flunarizine; hepronicate (U.S. Pat. No. 3,384,642); ifenprodil; iloprost (U.S. Pat. No. 4,692,464); inositol niacinate (Badgett et al., Journal of the American Chemical Society, 1947, 69, 2907); isoxsuprine (U.S. Pat. No. 3,056,836); kallidin (Nicolaides et al., Biochem. Biophys. Res. Commun., 1961, 6, 210); kallikrein (German Patent No. 1,102,973); moxisylyte (German Patent No. 905,738); nafronyl; nicametate; nicergoline; nicofaranose (Swiss Patent No. 366,523); nylidrin (U.S. Pat. Nos. 2,661,372 and 2,661,373); pentifylline; pentoxifylline (U.S. Pat. No. 3,422,107); piribedil (U.S. Pat. No. 3,299,067); prostaglandin E1 (Merck Index, Twelfth Edition, Budaveri, Ed, New Jersey 1996, page 1353); suloctidil (German Patent No. 2,334,404); tolazoline (U.S. Pat. No. 2,161,938); and xanthinol niacinate (German Patent No. 1,102,750). The disclosures of all such patents and references are incorporated herein by reference.

The term "diuretic" as used herein includes but is not limited to diuretic benzothiadiazine derivatives, diuretic organomercurials, diuretic purines, diuretic steroids, diuretic sulfonamide derivatives, diuretic uracils and other diuretics such as amanozine (Austrian Patent No. 168,063); amiloride (Belgium Patent No. 639,386); arbutin (Tschitschibabin et al., Annalen, 1930, 479, 303); chlorazanil (Austrian Patent No. 168,063); ethacrynic acid (U.S. Pat. No. 3,255,241); etozolin (U.S. Pat. No. 3,072,653); hydracarbazine (British Patent No. 856,409); isosorbide (U.S. Pat. No. 3,160,641); mannitol; metochalcone (Freudenberg et al., Ber., 1957, 90, 957); muzolimine (U.S. Pat. No. 4,018,890); perhexiline; ticrynafen (U.S. Pat. No. 3,758,506); triamterene (U.S. Pat. No. 3,081,230); and urea. The disclosures of all such patents and references are incorporated herein by reference. Diuretic benzothiadiazine derivatives within the scope of this invention include, but are not limited to: althiazide (British Patent No. 902,658); bendroflumethiazide (U.S. Pat. No. 3,392,168); benzthiazide (U.S. Pat. No. 3,440,244); benzyl hydrochlorothiazide (U.S. Pat. No. 3,108,097); buthiazide (British Patents Nos. 861,367 and 885,078); chlorothiazide (U.S. Pat. Nos. 2,809,194 and 2,937,169); chlorthalidone (U.S. Pat. No. 3,055,904); cyclopenthiazide (Belgium Patent No. 587,225); cyclothiazide (Whitehead et al Journal of Organic Chemistry, 1961, 26, 2814); epithiazide (U.S. Pat. No. 3,009,911); ethiazide (British Patent No. 861,367); fenquizone (U.S. Pat. No. 3,870,720); indapamide (U.S. Pat. No. 3,565,911); hydrochlorothiazide (U.S. Pat. No. 3,164,588); hydroflumethiazide (U.S. Pat. No. 3,254,076); methyclothiazide (Close et al., Journal of the American Chemical Society, 1960, 82, 1132); meticrane (French Patents Nos. M2790 and 1,365,504); metolazone (U.S. Pat. No. 3,360,518); paraflutizide (Belgium Patent No. 15 620,829); polythiazide (U.S. Pat. No. 3,009,911); quinethazone (U.S. Pat. No. 2,976,289); teclothiazide (Close et al., Journal of the American Chemical Society, 1960, 82, 1132); and trichlormethiazide (deStevens et al., Experientia, 1960, 16, 113). The disclosures of all such patents and references are incorporated herein by reference. Diuretic sulfonamide derivatives within the scope of this invention include, but are not limited to: acetazolamide (U.S. Pat. No. 2,554,816); ambuside (U.S. Pat. No. 3,188,329); azosemide (U.S. Pat. No. 3,665,002); bumetanide (U.S. Pat. No. 3,806,534); butazolamide (British Patent No. 769,757); chloraminophenamide (U.S. Pat. Nos. 2,909,194; 2,965,655; and 2,965,656); clofenamide (Olivier, Rec. Trav. Chim., 1918, 37, 307); clopamide (U.S. Pat. No. 3,459,756); clorexolone (U.S. Pat. No. 3,183,243); disulfamide (British Patent No. 851,287); ethozolamide (British Patent No. 795,174); furosemide (U.S. Pat. No. 3,058,882); mefruside (U.S. Pat. No. 3,356,692); methazolamide (U.S. Pat. No. 2,783,241); piretanide (U.S. Pat. No. 4,010,273); torsemide (U.S. Pat. No. 4,018,929); tripamide (Japanese Patent No. 305,585); and xipamide (U.S. Pat. No. 3,567,777). The disclosures of all such patents and references are incorporated herein by reference.

Selective neutral endopeptidase inhibitors are taught by Delaney et al. in U.S. Pat. Nos. 4,722,810 and 5,223,516 and the use of selective neutral endopeptidase inhibitors alone or in combination with angiotensin converting enzyme inhibitors to treat hypertension are disclosed by Delaney et al. U.K. Patent Application 2,207,351 and by Haslanger et al. in U.S. Pat. No. 4,749,688. Compounds possessing both neutral endopeptidase and angiotensin converting enzyme inhibition activity are disclosed by Flynn et al. in U.S. Pat. No. 5,366,973, European Patent Application 481,522 and PCT Patent Applications WO 93/16103, and WO 94/10193, Warshawsky et al. European Patent Applications 534,363, 534, 396 and 534,492, Fournie-Zaluski European Patent Application 524,553, Karanewsky et al. European Patent Application 599,444, Karanewsky European Patent Application 595,610, Robl et al., European Patent Application 629,627, Robl U.S. Pat. No. 5,362,727 and European Patent Application 657,453. The disclosures of all such patents and publications are incorporated herein by reference.

Further, the anti-hypertensive agents which may be used in accordance with this invention and the pharmaceutically acceptable salts thereof may occur as prodrugs, hydrates or solvates. Said hydrates and solvates are also within the scope of the present invention. Preferred anti-hypertensive agents of the invention include calcium channel blockers, A-II antagonists, ACE inhibitors and β-blockers. More preferred anti-hypertensive agents of the invention include ACE inhibitors, particularly lisinopril, enalapril and captopril, and A-II antagonists, particularly losartan. The anti-hypertensives described herein are generally commercially available, or they may be made by standard techniques including those described in the references cited above.

The instant compounds are also useful, alone, or in combination with ovulation stimulators such as, but not limited to; bromocriptine (e.g., PARLODEL), luprolide (e.g., LUPRON), clomifene (e.g., CLOMID, SEROPHENE) and pharmaceutically acceptable salts thereof, follicle stimulating hormone (e.g., FERTINEX/METRODIN, FOLLISTIM, GONAL F), chorionic gonadotropin (e.g., PROFASI, PREGNYL), luteinizing hormone releasing hormone (e.g., GONADORELIN), luteinizing hormone and combinations thereof to treat or prevent ovarian hyperstimulation syndrome (OHSS). OHSS is a side effect that occurs during infertility treatment with ovulation inducing drugs. OHSS has also been reported to occur as a result of increased endogenous seceretion of gonadotropins (*Obstet. Gynecol.* 21:28, 1963; *J. Obstet. Gynaecol. Br. Commonw.* 74:451, 1967). Symptoms of OHSS range from mild to critical and are associated with ovarian enlargement and increased vascular permeability. Women with the most severe symptoms demonstrate increased VEGF levels in follicular fluids that are reversed via the addition of a VEGF antibody indicating that VEGF is responsible for vascular permeability contributing to the pathogenesis of OHSS. Levin, E. R. et al., *J. Clin. Invest.* 102, 1978–1985 (1998). Therefore, a method of treating or preventing ovarian hyperstimulation syndrome, which comprises administering a therapeutically effective amount of a claimed compound, alone, or in combination with an ovulation stimulator is within the scope of the present invention.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmaceutically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invention therefore encompasses the use of the instantly claimed compounds in combination with a second agent selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be used as the second agent are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-(chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer which comprises administering a therapeutically effective amount of a claimed compound in combination with radiation therapy and/or in combination with an agent selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula I in combination with paclitaxel or trastuzumab.

The invention further encompasses a method of treating or preventing cancer which comprises administering a therapeutically effective amount of a claimed compound in combination with a COX-2 inhibitor.

These and other aspects of the invention will be apparent from the teachings contained herein.

Assays

The compounds of the instant invention described in the Examples were tested by the assays described below and were found to have kinase inhibitory activity. Other assays are known in the literature and could be readily performed by those of skill in the art (see, for example, Dhanabal et al., *Cancer Res.* 59:189–197; Xin et al., *J. Biol. Chem.* 274: 9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radiolabeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000× g and lysed at 4° C. for 30 minutes with 1/10 volume of lysis buffer followed by centrifugation at 100,000× g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.

2. Add 35 μl of reaction mix containing 5 μl of 10× reaction buffer, 5 μl 25 mM ATP/10 μCi[$^{33}$P]ATP (Amersham), and 5 μl 10× substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μl aliquot to filter plate.

8. Aspirate and wash 3 times with wash solution.

9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound two hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 1–5 below.

Culture Plates: NUNCLON 96-well polystyrene tissue culture plates (NUNC #167008).

Assay Medium: Dulbecco's modification of Eagle's medium containing 1 mg/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human VEGF$_{165}$ (500 ng/mL; R&D Systems) and bFGF (10 ng/mL; R&D Systems) are prepared in Assay Medium.

10×[$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) Na$_2$CO$_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% CO$_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% CO$_2$ for 2 hours to allow test compounds to enter cells.

3. After the 2-hour pretreatment period, cells are stimulated by addition of 10 μL/well of either Assay Medium, 10× VEGF solution or 10× bFGF solution. Cells are then incubated at 37° C. and 5% CO$_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of the present invention are inhibitors of VEGF and thus are useful for the inhibition of angio-genesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp. 915–924, December 1999).

III. Flt-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.
2. The appropriate amount of reaction mix was prepared at room temperature:
   10× Buffer (20 mM Tris pH 7.4/0.1 M NaCl/1 mM DTT final)
   0.1M MnCl$_2$ (5 mM final)
   pEY substrate (75 μg/mL)
   ATP/[$^{33}$P]ATP (2.5 μM/1 μCi final)
   BSA (500 μg/mL final).
3. 5 μL of the diluted inhibitor was added to the reaction mix. (Final volume of 5 μL in 50% DMSO). To the positive control wells, blank DMSO (50%) was added.
4. 35 μL of the reaction mix was added to each well of a 96 well plate.
5. Enzyme was diluted into enzyme dilution buffer (kept at 4° C.).
6. 10 μL of the diluted enzyme was added to each well and mix (5 nM final). To the negative control wells, 10 μL 0.5 M EDTA was added per well instead (final 100 mM).
7. Incubation was then carried out at room temperature for 30 minutes.
8. Stopped by the addition of an equal volume (50 μL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 μL per wash).
12. Allowed to dry under vacuum for 2–3 minutes.
13. Dryed in hood for ~20 minutes.
14. Assembled Wallac Millipore adapter and added 50 μL of scintillant to each well and counted.

IV. Flt-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:

1. Dilute inhibitors (account for the final dilution into the assay, 1:20)
2. Prepare the appropriate amount of reaction mix at room temperature.
   10× Buffer (20 mM Tris pH 7.4/0.1 M NaCl/1 mM DTT final)
   0.1M MnCl$_2$ (5 mM final)
   pEY substrate (75 μg/mL)
   ATP/[$^{33}$P]ATP (0.5 μM/L μCi final)

BSA (500 μg/mL final)
3. Add 5 μL of the diluted inhibitor to the reaction mix. (Final volume of 5 μL in 50% DMSO). Positive control wells—add blank DMSO (50%).
4. Add 35 μL of the reaction mix to each well of a 96 well plate.
5. Dilute enzyme into enzyme dilution buffer (keep at 4° C.).
6. Add 10 μL of the diluted enzyme to each well and mix (5–10 nM final). Negative control wells—add 10 μL 0.5 M EDTA per well instead (final 100 mM)
7. Incubate at room temperature for 60 min.
8. Stop by the addition of an equal volume (50 μL) of 30% TCA/0.1M Na pyrophosphate.
9. Incubate for 15 min to allow precipitation.
10. Transfer to Millipore filter plate.
11. Wash 3× with 15% TCA/0.1M Na pyrophosphate (125 μL per wash).
12. Allow to dry under vacuum for 2–3 min.
13. Dry in hood for ~20 min.
14. Assemble Wallac Millipore adapter and add 50 μL of scintillant to each well and count.

EXAMPLES

Examples provided are intended to assist in a further understanding of the invention. Particular materials employed, species and conditions are intended to be illustrative of the invention and not limiting of the reasonable scope thereof.

SCHEME 1

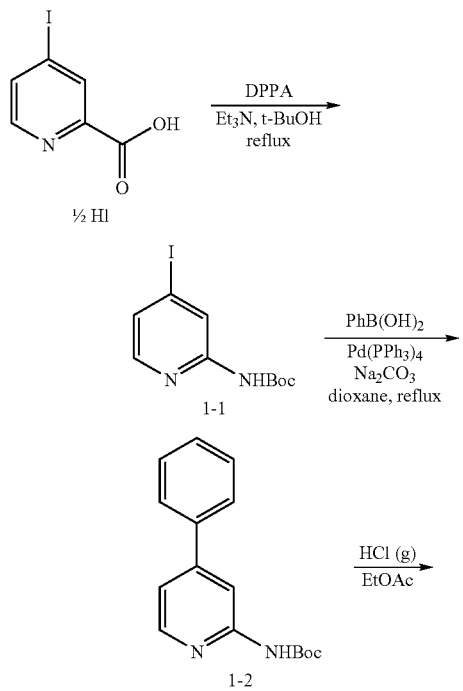

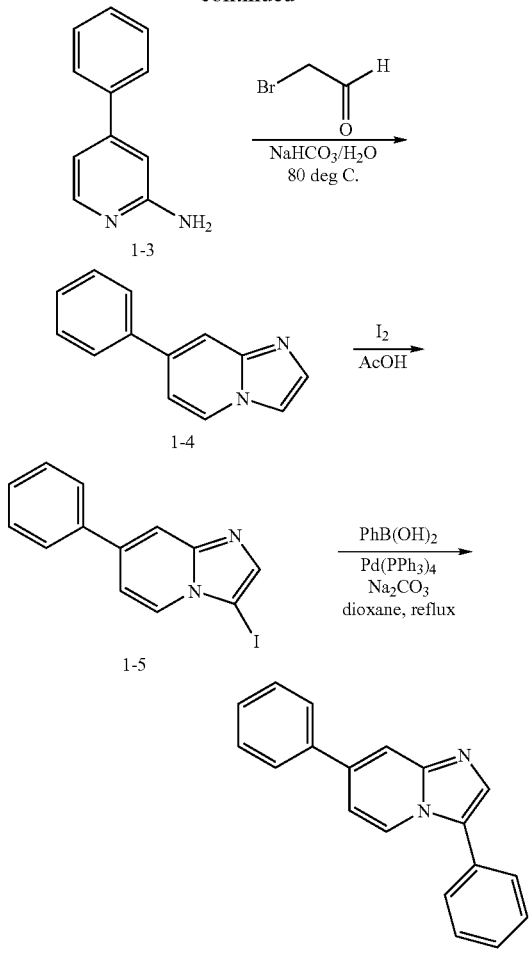

Step 1: tert-butyl 4-iodopyridin-2-ylcarbamate (1-1)

A solution of 4-iodopicilinic acid hemi-hydroiodide hydrate (prepared by the method of Lohse, *Synthetic Communications* 1996, 26, 2017–2025, 5.00 g, 16.0 mmol, 1 equiv), diphenylphosphoryl azide (5.72 g, 20.8 mmol, 1.30 equiv), and triethylamine (5.57 mL, 39.9 mmol, 2.50 equiv) in t-BuOH (200 mL) was heated at reflux for 2 h. The reaction mixture was concentrated, and the residue was partitioned between saturated aqueous sodium bicarbonate solution (300 mL) and ethyl acetate (300 mL). The organic layer was dried over sodium sulfate and concentrated. The residue was suspended in a 1:1 mixture of hexanes and ethyl acetate and filtered to give tert-butyl 4-iodopyridin-2-ylcarbamate (1-1) as a beige solid. $^1$H NMR (300 MHz, CDCl$_3$) δ 8.44 (s, 1H), 8.39 (s, 1H), 7.93 (d, 1H, J=5.1 Hz), 7.32 (dd, 1H, J=5.2, 1.2 Hz), 1.54 (s, 9H).

Step 2: tert-butyl 4-phenylpyridin-2-ylcarbamate (1-2)

Tetrakis(triphenylphosphine)palladium(0) (340 mg, 0.29 mmol, 0.050 equiv) was added to a deoxygenated mixture of tert-butyl 4-iodopyridin-2-ylcarbamate (1-1, 1.87 g, 5.84 mmol, 1 equiv), phenyl boronic acid (1.07 g, 8.76 mmol, 1.50 equiv), and aqueous saturated sodium carbonate solution (2.0 M, 8.8 mL, 18 mmol, 3.0 equiv) in dioxane (50 mL), and the resulting mixture was heated at reflux for 18 h. The reaction mixture was cooled then concentrated. The residue was partitioned between half-saturated aqueous NaCl solution (100 mL) and EtOAc (100 mL). The organic layer was dried over sodium sulfate, and concentrated. The residue was purified by flash column chromatography (dichloromethane, initially, grading to 40% EtOAc in dichloromethane) to give tert-butyl 4-phenylpyridin-2-ylcarbamate (1-2) as an off-white solid. LRMS m/z (M+H) Calcd: 214.3 (minus t-Bu), 171.3 (minus Boc); found 215.0 and 171.0.

Step 3: 4-phenylpyridin-2-amine (1-3)

A stream of HCl gas was bubbled into a suspension of tert-butyl 4-phenylpyridin-2-ylcarbamate (1–2, 0.93 g, 3.4 mmol, 1 equiv) in EtOAc (50 mL) at 0° C. for 2 min. The acidified solution was then heated at 60° C. for 3 h. The reaction mixture was cooled then concentrated to give 4-phenylpyridin-2-amine (1-3) as an off-white solid. LRMS m/z (M+H) Calcd: 171.2, found 170.9.

Step 4: 7-phenylimidazo[1,2-a]pyridine (1-4)

A mixture of bromoacetaldehyde diethyl acetal (0.88 mL, 5.9 mmol, 2.0 equiv) and concentrated HCl (0.1 mL, 0.4 equiv) in water (15 mL) was stirred at 23° C. for 2 h, then heated at 80° C. for 30 min. The mixture was allowed to cool to 23° C., and 4-phenylpyridin-2-amine (1-3, 0.50 g, 2.9 mmol, 1 equiv) and NaHCO$_3$ (0.59 g, 7.1 mmol, 2.4 equiv) were added. The resulting mixture was then heated to 50° C. where MeOH (2 mL) and dioxane (3 mL) were added to increase solubility. The reaction mixture was stirred at 50° C. for 18 h, then concentrated. The residue was partitioned between EtOAc (200 mL) and brine (200 mL). The organic layer was concentrated to provide 7-phenylimidazo[1,2-a]pyridine (1-4) as a brown solid. $^1$H NMR (300 MHz, CDCl$_3$) δ 8.18 (d, 1H, J=7.3 Hz), 7.84 (s, 1H), 7.67 (s, 1H), 7.66 (s, 2H, J=7.3 Hz), 7.60 (s, 1H), 7.49 (t, 2H, J=7.5 Hz), 7.40 (t, 1H, J=7.3 Hz), 7.09 (dd, 1H, J=7.0, 1.2 Hz).

Step 5: 3-iodo-7-phenylimidazo[1,2-a]pyridine (1-5)

A solution of 7-phenylimidazo[1,2-a]pyridine (1-4, 110 mg, 0.56 mmol, 1 equiv) and iodine (140 mg, 0.56 mmol, 1.0 equiv) in acetic acid (4 mL) was stirred at 23° C. for 18 h. More iodine (130 mg) was added and the mixture was stirred for 24 h at 70° C. A third portion of iodine (130 mg) was added and heating (70° C.) was continued for 2 h. The reaction mixture was basified with aqueous saturated sodium bicarbonate solution (100 mL), and the remaining iodine was quenched with addition of aqueous saturated sodium thiosulfate solution (10 mL). The mixture was extracted with EtOAc (100 mL), and the organic layer was washed with brine, dried over sodium sulfate, and then concentrated to give 3-iodo-7-phenylimidazo[1,2-a]pyridine (1-5) as a light-brown solid. $^1$H NMR (300 MHz, CDCl$_3$) δ 8.18 (d, 1H, J=7.3 Hz), 7.82 (s, 1H), 7.73 (s, 1H), 7.67 (m, 2H), 7.50 (t, 2H, J=7.3 Hz), 7.42 (t, 1H, J=7.3 Hz), 7.23 (d, 1H, J=7.0 Hz).

Step 6: 3,7-diphenylimidazo[1,2-a]pyridine (1-6)

Tetrakis(triphenylphosphoine)palladium(0) (16 mg, 0.014 mmol, 0.050 equiv) was added to a deoxygenated mixture of 3-iodo-7-phenylimidazo[1,2-a]pyridine (1-5, 88 mg, 0.28 mmol, 1 equiv), phenyl boronic acid (50 mg, 0.41 mmol, 1.5 equiv), and aqueous saturated sodium carbonate solution (0.42 mL, 3.0 equiv) in dioxane (5 mL), and the resulting mixture was heated at reflux for 18 h. The reaction mixture was cooled, then concentrated, and the residue was partitioned between half-saturated aqueous NaCl solution (50 mL) and EtOAc (50 mL). The organic layer was dried over sodium sulfate and concentrated. The residue was purified by flash column chromatography (dichloromethane, initially, grading to 40% EtOAc in dichloromethane) to give 3,7-diphenylimidazo[1,2-a]pyridine (1-6) as a tan solid. $^1$H NMR (300 MHz, CDCl$_3$) δ 8.41 (dd, 1H, J=7.2, 0.6 Hz), 7.90 (dd, 1H, J=1.8, 0.6 Hz), 7.74 (s, 1H), 7.69 (m, 2H), 7.62–7.39 (m, 8H), 7.12 (dd, 1H, J=7.0, 1.8 Hz).

The following compounds were prepared by simple modifications of the above procedures.

| Compound | Structure | Name | LRMS m/z (M + H) |
|---|---|---|---|
| 1-7 | 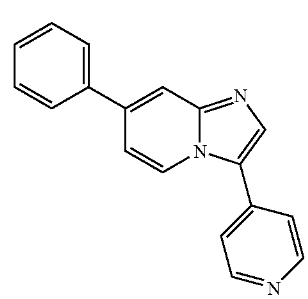 | 7-phenyl-3-pyridin-4-ylimidazo[1,2-a]pyridine | 272.0 |

-continued

| Compound | Structure | Name | LRMS m/z (M + H) |
|---|---|---|---|
| 1-8 | 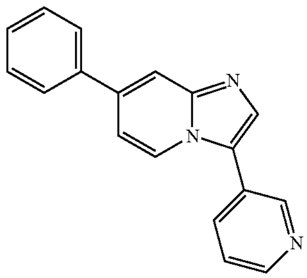 | 7-phenyl-3-pyridin-3-ylimidazo[1,2-a]pyridine | 272.0 |
| 1-9 | 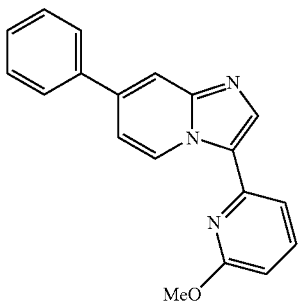 | 3-(6-methoxypyridin-2-yl)-7-phenylimidazo[1,2-a]pyridine | 302.0 |
| 1-10 | 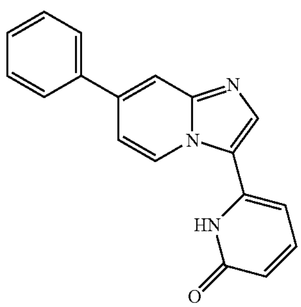 | 6-(7-phenylimidazo[1,2-a]pyridin-3-yl)pyridin-2(1H)-one | 288.0 |
| 1-11 | 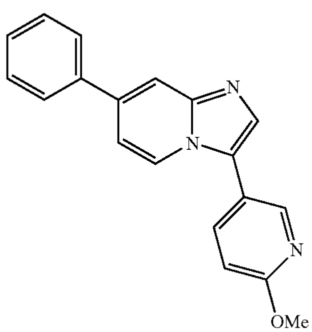 | 3-(6-methoxypyridin-3-yl)-7-phenylimidazo[1,2-a]pyridine | 302.0 |
| 1-12 | 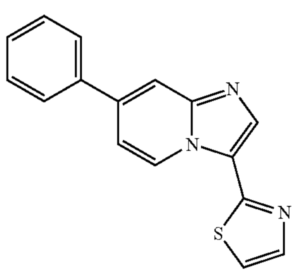 | 7-phenyl-3-(1,3-thiazol-2-yl)imidazo[1,2-a]pyridine | 278.1 |

SCHEME 2

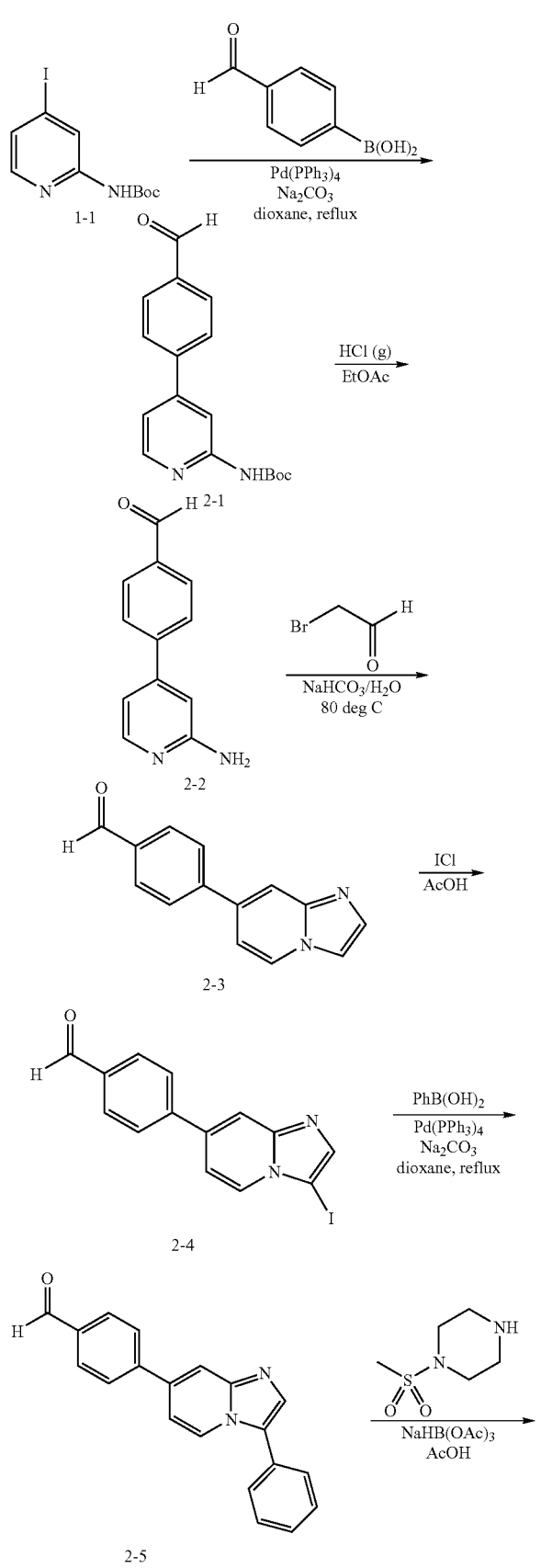

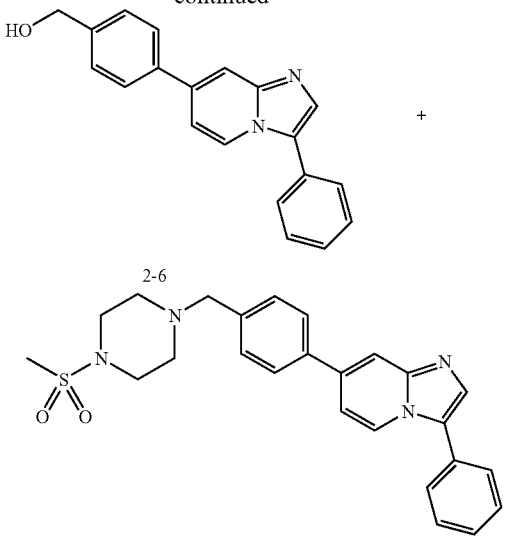

Step 1: tert-butyl 4-(4-formylphenyl)pyridin-2-ylcarbamate (2-1)

Tetrakis(triphenylphosphine)palladium(0) (90 mg, 0.08 mmol, 0.05 equiv) was added to a deoxygenated mixture of tert-butyl 4-iodopyridin-2-ylcarbamate (1-1, 0.500 g, 1.56 mmol, 1 equiv), 4-formylphenyl boronic acid (351 mg, 2.34 mmol, 1.50 equiv), and aqueous saturated sodium carbonate solution (2.0 M, 2.3 mL, 4.7 mmol, 3.0 equiv) in dioxane (15 mL), and the resulting mixture was heated at reflux for 18 h. The reaction mixture was cooled then concentrated. The residue was partitioned between half-saturated aqueous NaCl solution (100 mL) and EtOAc (100 mL). The organic layer was dried over sodium sulfate, and concentrated to give tert-butyl 4-(4-formylphenyl)pyridin-2-ylcarbamate (2-1) as an off-white solid. LRMS m/z (M+H) Calcd: 242.2 (minus t-Bu), 199.2 (minus Boc); found 243.0 and 199.0.

Step 2: 4-(2-aminopyridin-4-yl)benzaldehyde (2-2)

A stream of HCl gas was bubbled into a suspension of tert-butyl 4-(4-formylphenyl)pyridin-2-ylcarbamate (2-1, 486 mg, 1.63 mmol) in EtOAc (50 mL) at 0° C. for 2 min. The acidified solution was allowed to reach 23° C. and was then stirred for 18 h. The reaction mixture was concentrated to give 4-(2-aminopyridin-4-yl)benzaldehyde (2-2) as an off-white solid. $^1$H NMR (300 MHz, CDCl$_3$) δ 10.07 (s, 1H), 8.18 (d, 1H, J=5.5 Hz), 7.97 (d, 2H, J=8.6 Hz), 7.74 (d, 2H, J=8.1 Hz), 6.91 (dd, 1H, J=5.5, 1.5 Hz), 6.73 (s, 1H), 4.61 (s, 2H).

Step 3: 4-imidazo[1,2-a]pyridin-7-ylbenzaldehyde (2-3)

A mixture of bromoacetaldehyde diethyl acetal (0.49 mL, 23.3 mmol, 2.0 equiv) and concentrated HCl (0.05 mL, 0.4 equiv) in water (10 mL) was stirred at 23° C. for 2 h, then heated at 80° C. for 30 min. The mixture was allowed to cool to 23° C., and 4-(2-aminopyridin-4-yl)benzaldehyde (2-2, 323 mg, 1.63 mmol, 1 equiv) and NaHCO$_3$ (324 mg, 3.91 mmol, 2.40 equiv) were added. The resulting mixture was then heated to 50° C. where MeOH (2 mL) and dioxane (3 mL) were added to increase solubility. The reaction mixture was stirred at 50° C. for 18 h, then concentrated. The residue was partitioned between EtOAc (200 mL) and brine (200 mL). The organic layer was concentrated to provide 4-imidazo[1,2-a]pyridin-7-ylbenzaldehyde (2-3) as a brown solid. LRMS m/z (M+H) Calcd: 223.2, found 223.0.

Step 4: 4-(3-iodoimidazo[1,2-a]pyridin-7-yl)benzaldehyde(2-4)

A solution of 4-imidazo[1,2-a]pyridin-7-ylbenzaldehyde (2-3, 2.09 g, 9.40 mmol, 1 equiv) and iodine monochloride (3.05 g, 18.8 mmol, 2.00 equiv) in acetic acid (50 mL) was stirred at 23° C. for 2 h. The reaction mixture was basified with aqueous saturated sodium bicarbonate solution (200 mL), and the remaining iodine monochloride was quenched with addition of aqueous saturated sodium thiosulfate solution (100 mL). The mixture was extracted with EtOAc (400 mL), and the organic layer was washed with brine, dried over sodium sulfate, and then concentrated to give 4-(3-iodoimidazo[1,2-a]pyridin-7-yl)benzaldehyde(2-4) as a light-brown solid. $^1$H NMR (300 MHz, CDCl$_3$) δ 10.09 (s, 1H), 8.28 (dd, 1H, J=7.3, 0.9), 8.01 (d, 2H, J=7.7), 7.90 (dd, 1H, J=1.6, 0.9), 7.84 (d, 2H, J=8.2), 7.78 (s, 1H), 7.60 (m obscured by CHCl$_3$ peak, 1H).

Step 5: 4-(3-phenylimidazo[1,2-a]pyridin-7-yl)benzaldehyde (2-5)

Tetrakis(triphenylphosphoine)palladium(0) (92 mg, 0.080 mmol, 0.050 equiv) was added to a deoxygenated mixture of 4-(3-iodoimidazo[1,2-a]pyridin-7-yl)benzaldehyde (2-4, 555 mg, 1.94 mmol, 1 equiv), phenyl boronic acid (486 mg, 3.99 mmol, 2.50 equiv), and aqueous saturated sodium carbonate solution (2.4 mL, 3.0 equiv) in dioxane (20 mL), and the resulting mixture was heated at reflux for 4 h. Additional tetrakis(triphenylphosphoine)palladium(0) (100 mg, 0.09 mmol, 0.05 equiv), phenyl boronic acid (500 mg, 4.0 mmol, 2.5 equiv), aqueous saturated sodium carbonate solution (2.5 mL, 3.1 equiv), and lithium chloride (200 mg, 5 mmol, 3 equiv) were added and the mixture was heated at reflux for 18 h. The reaction mixture was cooled, then concentrated, and the residue was partitioned between half-saturated aqueous NaCl solution (100 mL) and EtOAc (6×100 mL). The combined organic layers were dried over sodium sulfate and concentrated. The residue was purified by reverse-phase liquid chromatography (H$_2$O/CH$_3$CN gradient w/0.1% TFA) to give 4-(3-phenylimidazo[1,2-a]pyridin-7-yl)benzaldehyde (2-5) as a tan solid. LRMS m/z (M+H) Calcd 299.3, found 298.9.

Step 6: [4-(3-phenylimidazo[1,2-a]pyridin-7-yl)phenyl]methanol (2-6) and 7-(4-{[4-(methylsulfonyl)piperazin-1-yl]methyl}phenyl)-3-phenylimidazo[1,2-a]pyridine (2-7)

A mixture of 4-(3-phenylimidazo[1,2-a]pyridin-7-yl)benzaldehyde (2-5, 75 mg, 0.25 mmol, 1 equiv), 4-(methylsulfonyl)piperazine (49 mg, 0.30 mmol, 1.2 equiv), sodium triacetoxyborohyridide (64 mg, 0.30 mmol, 1.2 equiv), acetic acid (14 μL, 0.25 mmol, 1.0 equiv), and 4-angstrom molecular sieves (50 mg) in 1,2-dichloroethane (5 mL) was stirred at 23° C. for 18h. The reaction mixture was filtered, and the filtrate concentrated. The residue was purified by reverse-phase liquid chromatography (H$_2$O/CH$_3$CN gradient w/0.1% TFA) to provide [4-(3-phenylimidazo[1,2-a]pyridin-7-yl)phenyl]methanol (2-6) and 7-(4-{[4-(methylsulfonyl)piperazin-1-yl]methyl}phenyl)-3-phenylimidazo[1,2-a]pyridine (2-7).

$^1$H NMR (500 MHz, CD$_3$OD) δ$_{(2-6)}$ 8.76 (d, 1H, J=7.1 Hz), 8.16 (s, 1H), 8.13 (s, 1H), 7.88 (d, 2H, J=8.3 Hz), 7.83 (dd, 1H, J=7.1, 1.7 Hz), 7.75 (m, 2H), 7.66 (m, 3H), 7.58 (d, 2H, J=8.1 Hz), 4.71 (s, 2H), 3.34 (s, 1H). δ$_{(2-7)}$ 8.81 (d, 1H, J=7.1 Hz), 8.25 (s,1H), 8.19 (s, 1H), 8.03 (d, 2H, J=7.8 Hz), 7.85 (d, 1H, J=6.8 Hz), 7.76 (d, 4H, J=7.3 Hz), 7.67 (m, 3H), 4.48 (s, 2H), 3.55 (br s, 4H), 3.42 (br s, 4H), 2.95 (s, 3H).

The following compounds were prepared by simple modifications of the above procedures.

| Compound | Structure | Name | LRMS m/z (M + H) |
|---|---|---|---|
| 2-8 | 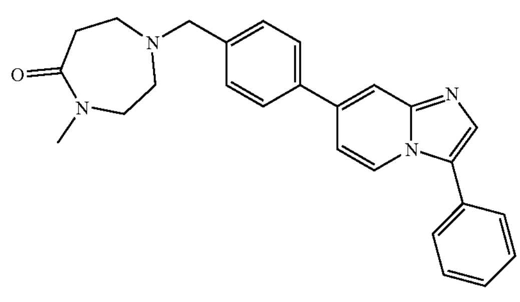 | 4-methyl-1-[4-(3-phenylimidazol[1,2-a]pyridin-7-yl)benzyl]-1,4-diazepan-5-one | 411.1 |

-continued
| Compound | Structure | Name | LRMS m/z (M + H) |
|---|---|---|---|
| 2-9 | 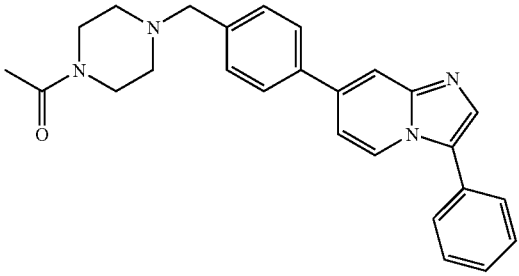 | 7-{4-[(4-acetylpiperazin-1-yl)methyl]phenyl}-3-phenylimidazo[1,2-a]pyridine | 411.1 |
| 2-10 | 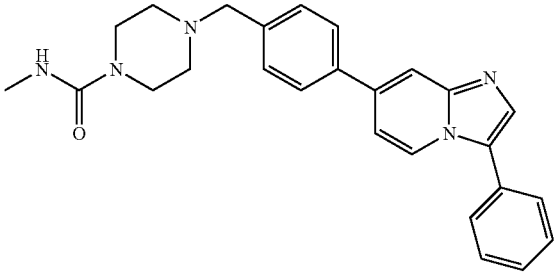 | N-methyl-4-[4-(3-phenylimidazo[1,2-a]pyridin-7-yl)benzyl]piperazine-1-carboxamide | 426.1 |
| 2-11 | 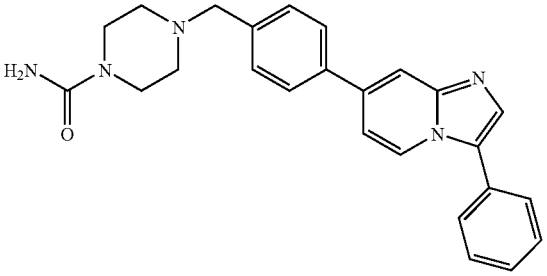 | 4-[4-(3-phenylimidazo[1,2-a]pyridin-7-yl)benzyl]piperazine-1-carboxamide | 412.1 |
| 2-12 | 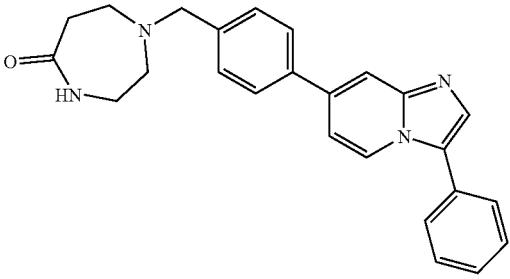 | 1-[4-(3-phenylimidazo[1,2-a]pyridin-7-yl)benzyl]-1,4-diazepan-5-one | 397.1 |
| 2-13 | 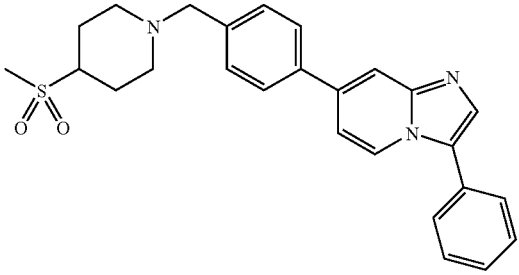 | 7-(4-{[4-(methylsulfonyl)piperidin-1-yl]methyl}phenyl)-3-phenylimidazol[1,2-a]pyridine | 446.1 |

SCHEME 3

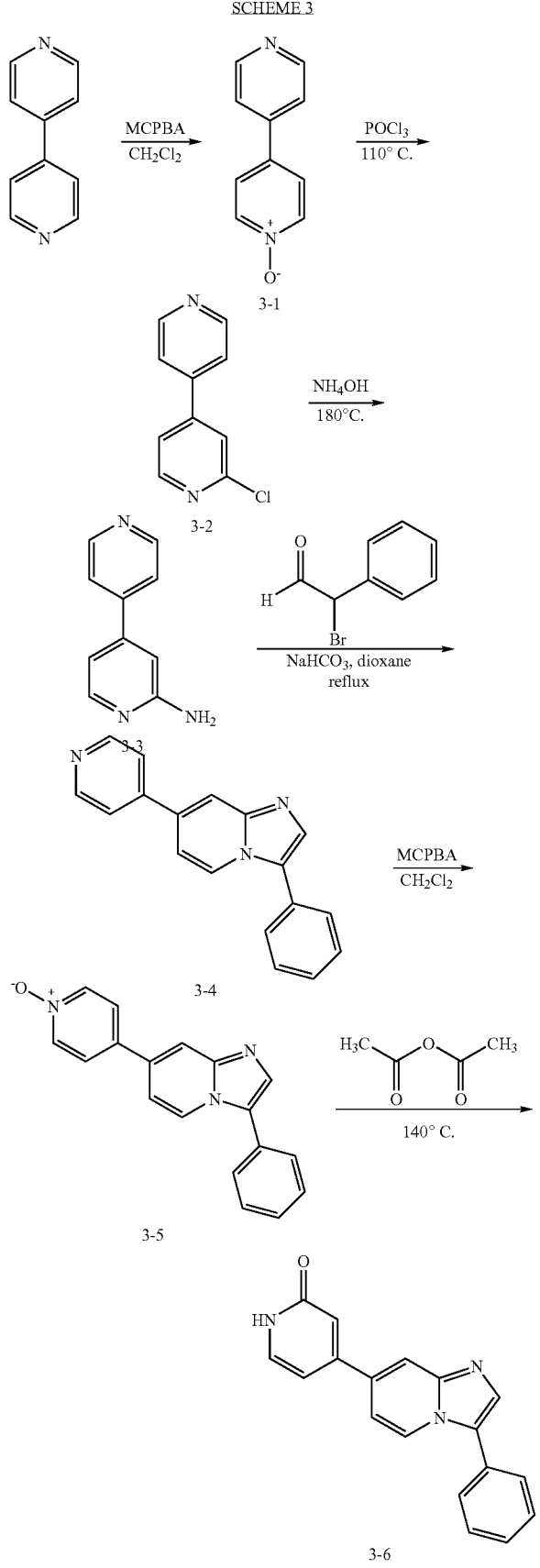

Step 1: 4,4'-bipyridine-1-oxide (3-1)

To the solution of 4,4'-bipyridine (25.00 g, 160.08 mmol, 1 equiv) in $CH_2Cl_2$ (200 mL) at 0° C. was added 3-chloroperoxybenzoic acid (35.87 g, 77%, 160.06 mmol, 1 equiv). The reaction mixture was stirred overnight at rt. The solid was filtered off and the filtrate was concentrated and purified by flash column chromatography (acetone to 10% MeOH in acetone) to give 4,4'-bipyridine-1-oxide (3-1) as a solid. $^1$H NMR ($CDCl_3$) δ 8.75 (d, 2H, J=5.9), 8.31 (d, 2H, J=7.1), 7.57 (d, 2H, J=7.0), 7.50(d, 2H, J=6.1).

Step 2: 2-chloro-4,4'-bipyridine (3-2)

The suspension of 4,4'-bipyridine-1-oxide (8.50 g, 49.36 mmol) in phosphorus oxychloride (80 mL) was heated to 110° C. overnight. The mixture was concentrated and the residue was treated with saturated aqueous $NaHCO_3$ solution (150 mL) slowly and then $Na_2CO_3$ solution (2M) until it was basic. The alkaline solution was extracted with chloroform (4×300 mL). The combined organic layer was dried, treated with activated carbon and filtered through celite. The filtrate was concentrated and the resulting solid was purified by flash column chromatography (4% MeOH in $CH_2Cl_2$) to give 2-Chloro-4,4'-bipyridine (3-2) as a off-yellow solid. $^1$H NMR ($CDCl_3$) δ 8.77 (dd, 2H, J=4.5, 1.6), 8.53 (d, 1H, J=5.1), 7.58 (s, 1H), 7.52 (dd, 2H, J=4.7, 1.7), 7.46 (dd, 1H, J=5.2, 1.5).

Step 3: 2-amino-4,4'-bipyridine (3-3)

The mixture of 2-chloro-4,4'-bipyridine (2.40 g, 12.59 mmol) and concentrated ammonium hydroxide (100 mL) in a steel bomb was heated to 180° C. for 36 h. The volatiles were then removed in vacuo to give 2-amino-4,4'-bipyridine as a solid. $^1$H NMR ($CDCl_3$) δ 8.71 (m, 2H), 8.18 (d, 1H, J=5.3), 7.48 (m, 2H), 6.8 (m, 1H), 6.72 (s, 1H). LRMS m/z (M+H) Calcd: 172.2, found: 172.2.

Step 4: 3-phenyl-7-(4-pyridyl)imidazo[1,2-a]pyridine (3-4)

To the solution of 2-amino-4,4'-bipyridine (0.482 g, 2.815 mmol, 1 equiv) in dioxane (14 mL) was added bromophenylacetaldehyde (0.897 g, 4.50 mmol, 1.6 equiv) and $NaHCO_3$ (0.473 g, 5.63 mmol, 2 equiv). The suspension was stirred at rt for 30 min and then heated to 80° C. for 6 h. The reaction mixture was poured into water and extracted with EtOAc. The combined organic layer was dried, concentrated and purified by flash column chromatography (5% MeOH in $CH_2Cl_2$) to give 3-phenyl-7-(4-pyridyl)imidazo[1,2-a]pyridine as a solid. $^1$H NMR ($CDCl_3$) δ 8.72 (d, 2H, J=6.1), 8.45 (d, 1H, J=7.3), 8.00 (s, 1H), 7.80 (s, 1H), 7.61–7.55 (m, 6H), 7.48–7.44 (m, 1H), 7.14 (d, 1H, J=7.3); LRMS m/z (M+H) Calcd: 272.3, found: 272.2.

Step 5: 7-(1-oxy-pyridin-4-yl)-3-phenyl-imidazo[1,2-a]pyridine (3-5)

To the solution of 3-phenyl-7-(4-pyridyl)imidazo[1,2-a]pyridine (0.175 g, 0.645 mmol, 1 equiv) in $CH_2Cl_2$ (7 mL) at 0° C. was added 3-chloroperoxybenzoic acid (0.144 g, 77%, 0.65 mmol, 1 equiv). The solution was stirred overnight and more 3-chloroperoxybenzoic acid (0.12 g, 77%) was added. After 4 h, the reaction mixture was purified by flash column chromatography (5%–10% MeOH in $CH_2Cl_2$) to give 7-(1-oxy-pyridin-4-yl)-3-phenyl-imidazo[1,2-a]pyridine as a solid. $^1$H NMR δ (CDCl$_3$) 8.42 (d, 1H, J=7.2), 8.28 (d, 2H, J=6.9), 7.93 (s, 1H), 7.80 (s, 1H), 7.61–7.54 (m, 6H), 7.49–7.45 (m, 1H), 7.06 (d, 1H, J=7.1). LRMS m/z (M+H) Calcd: 288.3, found: 288.0.

Step 6: 4-(3-phenyl-imidazo[1,2-a]pyridin-7-yl)-1H-pyridin-2-one (3-6)

The suspension of 7-(1-oxy-pyridin-4-yl)-3-phenyl-imidazo[1,2-a]pyridine (0.117 g, 0.407 mmol, 1 equiv) in acetic anhydride (2.0 mL) was heated to 140° C. overnight. The mixture was concentrated in vacuo. The residue was dissolved in MeOH (2 mL) and added concentrated NH$_4$OH (0.2 mL). The solution was stirred at rt for 2 h. The reaction mixture was then concentrated. The resulting residue was purified by flash column chromatography (5%–10% MeOH in CH$_2$Cl$_2$) to give 4-(3-phenyl-imidazo[1,2-a]pyridin-7-yl)-1H-pyridin-2-one as a solid. $^1$H NMR (CDCl$_3$) δ 8.44 (d, 1H, J=7.1), 7.95 (s, 1H), 7.80 (s, 1H), 7.61–7.54 (m, 4H), 7.48–7.45 (m, 2H), 7.07(dd, 1H, J=7.4, 1.5), 6.88 (s, 1H), 6.63 (dd, 1H, J=6.8, 1.7); LRMS m/z (M+H) Calcd: 288.3, found: 288.2.

SCHEME 4

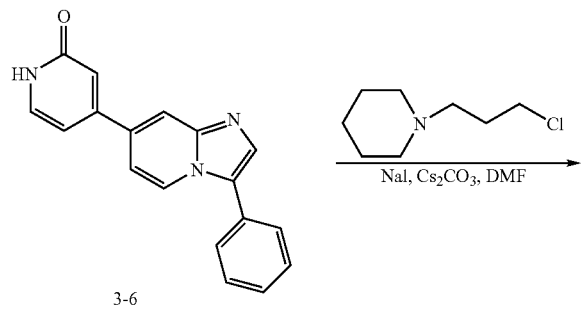

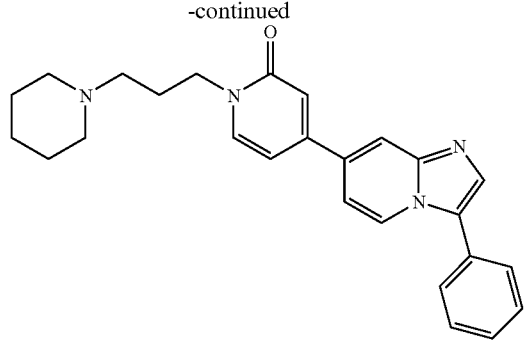

4-1

4-(3-phenylimidazo[1,2-a]pyridin-7-yl)-1-(3-piperidin-1-ylpropyl)pyridin-2(1H)-one To a solution of 4-(3-phenylimidazo[1,2-a]pyridin-7-yl)pyridin-2(1H)-one (0.050 g, 0.173 mmol) in 1.0 mL of anhydrous DMF was added sodium iodide (0.038 g, 0.260 mmol), cesium carbonate (0.140 g, 0.430 mmol), and 1-(3-chloropropyl)piperidine (0.0420 g, 0.25 mmol). Reaction was refluxed at 40° C. overnight. Poured reaction into saturated sodium bicarbonate solution and extracted with methylene chloride. Dried organic over sodium sulfate. Removed solvent under reduced pressure. Purified by silica chromatography (10% MeOH/CH$_2$Cl$_2$). $^1$H NMR (CDCl$_3$) δ 8.40 (d, 1H, J=6.59 Hz), 7.92 (s, 1H), 7.78 (s, 1H), 7.62–7.52 (m, 4H), 7.50 (d, 1H, J=7.09 Hz), 7.45 (t, 1H, J=7.33 Hz), 7.06 (dd, 1H, J=7.08, 1.71 Hz), 6.84 (s, 1H), 6.50 (dd, 1H, J=7.08, 2.20 Hz), 4.08 (t, 2H, J=6.84 Hz), 2.40 (bs, 2H), 2.02 (bs, 2H), 1.62 (bs, 8H), 1.46 (bs, 2H). HRMS m/z (M+1) Calc: 413.2, found: 413.3.

The following compounds were prepared by simple modifications of the above procedures.

| Compound | Structure | Name | LRMS m/z (M + H) |
|---|---|---|---|
| 4-2 | 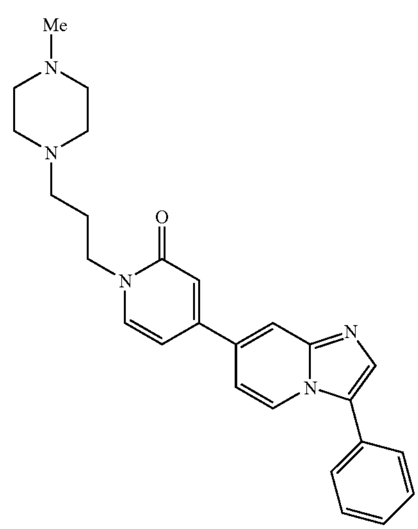 | 1-[3-(4-methylpiperazin-1-yl)propyl]-4-(3-phenylimidazo[1,2-a]pyridin 7-yl)pyridin-2(1H)-one | 428.0 |

| Compound | Structure | Name | LRMS m/z (M + H) |
|---|---|---|---|
| 4-3 | 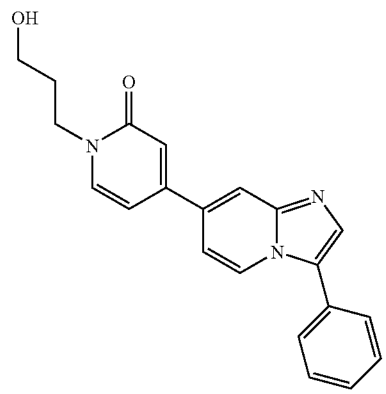 | 1-(3-hydroxypropyl)-4-(3-phenylimidazo[1,2-a]pyridin-7-yl)pyridin-2(1H)-one | 346.1542 |
| 4-4 | 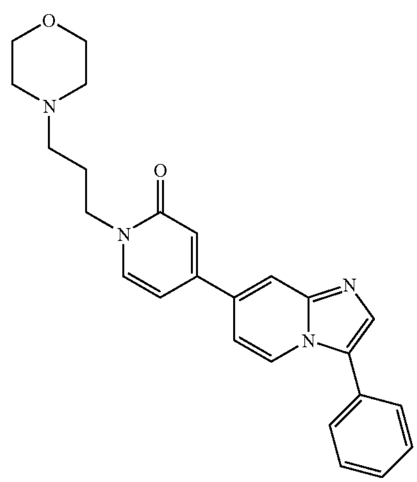 | 1-(3-morpholin-4-ylpropyl)-4-(3-phenylimidazo[1,2-a]pyridin-7-yl)pyridin-2(1H)-one | 415.2127 |
| 4-5 | 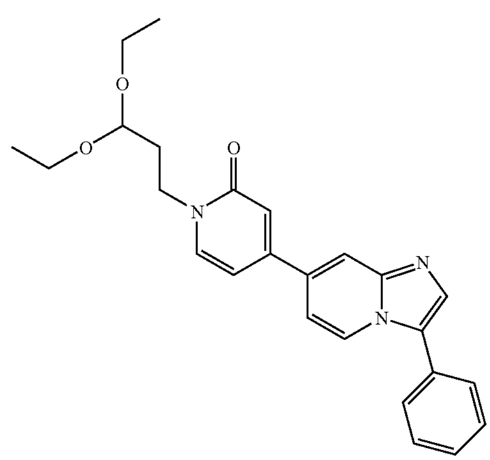 | 1-(3,3-diethoxypropyl)-4-(3-phenylimidazo[1,2-a]pyridin-7-yl)pyridin-2(1H)-one | 418.0 |

SCHEME 5

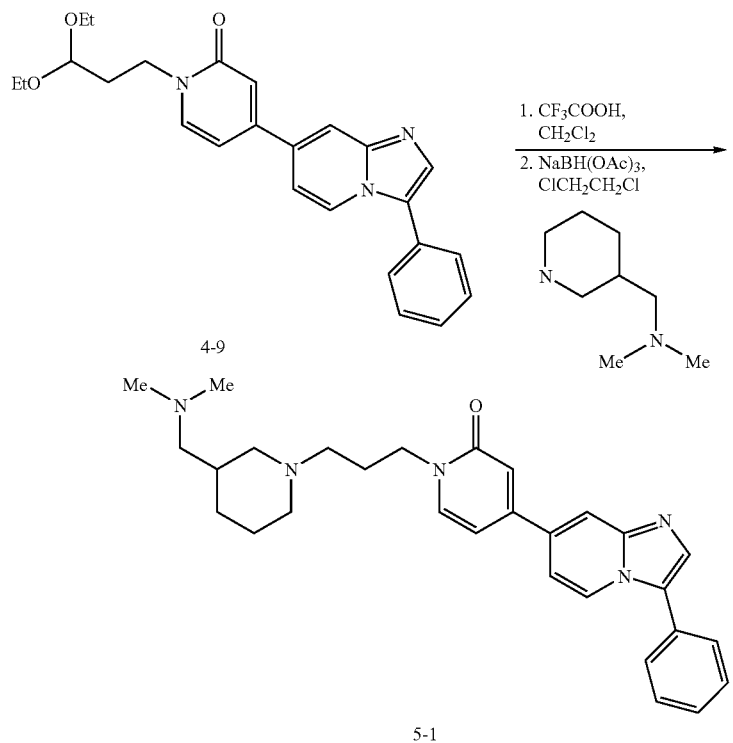

1-(3-{3-[(dimethylamino)methyl]piperidin-1-yl}propyl)-4-(3-phenylimidazo[1,2-a]pyridin-7-yl)pyridin-2(1H)-one To a solution of 4-(3-phenylimidazo[1,2-a]pyridin-7-yl)-1-(3-piperidin-1-ylpropyl)pyridin-2(1H)-one (0.210 g, 0.503 mmol) in 5.0 mL of a 2:1 solution of chloroform:(50% trifluoracetic acid:water) at 0° C. After 1 hour solvent was removed under reduced pressure to give 3-[2-oxo-4-(3-phenylimidazo[1,2-a]pyridin-7-yl)pyridin-1(2H)-yl]propanal. $^1$H NMR (CDCl$_3$) δ 8.94 (s, 1H), 8.90 (d, 1H, J=6.84 Hz), 8.05 (s, 1H), 7.73–7.64 (m, 6H), 7.60 (m, 4H), 4.90 (t, 2H, J=5.13 Hz), 2.60 (m, 2H). LCMS m/z (M+1) Calc: 344.1, found 344.0

To a solution of 3-[2-oxo-4-(3-phenylimidazo[1,2-a]pyridin-7-yl)pyridin-1(2H)-yl]propanal (0.035 g, 0.102 mmol) in 1.0 mL of 1,2-dichloroethane was added acetic acid (0.01 mL, 0.12 mol), 1,1'-biphenyl-3,4-diamine (0.160 g, 0.11o mmol), and sodium triacetoxyborohydride (0.030 g, 0.140 mmol). Reaction was stirred at room temperature overnight. Poured reaction into saturated sodium bicarbonate solution and extracted with methylene chloride. Removed solvent under reduced pressure. Purified by silica chromatography (0.5% NH$_4$OH/10% MeOH/CH$_2$Cl$_2$). $^1$H NMR (CDCl$_3$) δ 8.20 (d, 1H, J=7.08 Hz), 7.93 (s, 1), 7.80 (s, 1H), 7.60–7.52 (m, 4H), 7.50–7.42 (m, 2H), 7.06 (d, 1H, J=7.32 Hz), 6.84 (s, 1H), 6.44 (d, 1H, J=6.33 Hz), 4.02 (t, 2H, J=6.35 Hz), 2.35 (bs, 2H), 2.20 (s, 2H), 2.04 (m, 4H), 1.75 (m, 6H), 1.63 (s, 6H). LCMS m/z (M+1) Calc. 470.3, found 470.2.

SCHEME 6

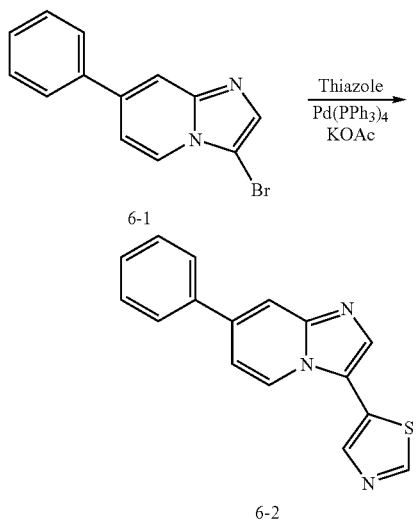

Step 1: 3-bromo-7-phenylimidazo[1,2-a]pyridine (6-1)

7-Phenylimidazo[1,2-a]pyridine (1-4, 0.284 g, 1.46 mmol) was dissolved in 5 ml of acetic acid. Bromine (0.075 ml, 1.46 mmol) was added dropwise. A tan solid rapidly formed in reaction mixture with concomitant dissapearance of orange-red bromine color. After 30 min the reaction was concentrated in vacuo and the residual solid was treated with saturated aqueous NaHCO₃ and was sonicated to break up clumps. Filtration, washing with water and air drying afforded 0.390 g of a yellow solid.

Step 2: 7-phenyl-3-(1,3-thiazol-5-yl)imidazo[1,2-a]pyridine (6-2)

A microwave vessel was charged with 3-bromo-7-phenylimidazo[1,2-a]pyridine (6-1, 0.050 g, 0.183 mmol), thiazole (0.065 ml, 0.92 mmol), tetrakis(triphenylphosphine)palladium(0) (0.011 g, 0.10 mmol) and KOAc (0.054 g, 0.55 mmol). N,N-dimethylacetamide, 1.5 ml, was added and the reaction was placed in the microwave reactor. The reaction was heated to 200° C. for 10 min. The reaction was diluted with water, and extracted 3× with DCM. The extracts were dried over Na₂SO₄, filtered and concentrated. The resulting residue was dissolved in DMSO and purified by reverse phase preparative HPLC. The resulting oil was triturated with ether, resulting in the rapid crystallization to a white solid. The solid was filtered and washed with ether. Afforded the pure title compound. ¹H NMR (CDCl₃) δ 9.11 (s, 1H), 8.47 (s, 1H), 8.37 (d, 1H, J=7.4 Hz), 8.20 (s, 1H), 8.00 (s, 1H), 7.73 (d, 2H, J=7.3 Hz), 7.57–7.52 (m, 4H). LCMS m/z (M+1) Calc: 278.1, found 278.1.

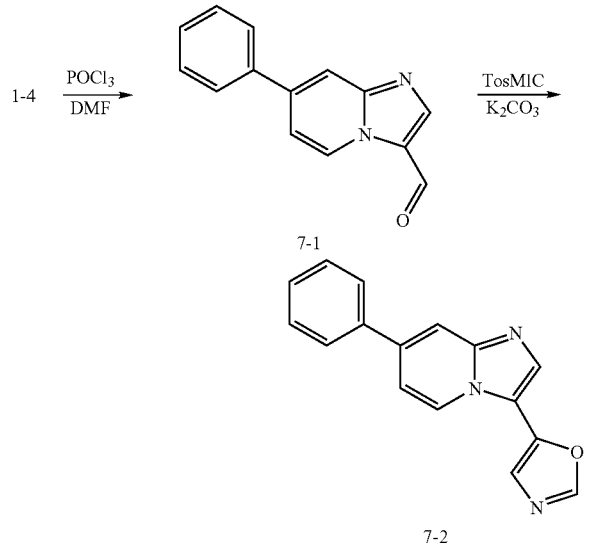

Step 1: 7-phenylimidazo[1,2-a]pyridine-3-carbaldehyde (7-1)

An oven dried flask under N2 was charged with 2 ml of N,N-dimethylformamide and phosphorous oxychloride (0.048 ml, 0.52 mmol) was added dropwise. 7-Phenylimidazo[1,2-a]pyridine (1-4, 0.100 g, 0.515 mmol) was added and the reaction was heated to 90° C. After 4 h additional POCl₃ (0.048 ml, 0.52 mmol) was added and the reaction was heated overnight. Another sample of POCl₃ (0.048 ml, 0.52 mmol) was added and heating was continued. After 4 h more, the reaction was cooled to ambient temperature. The reaction was quenched with saturated aqueous NaHCO₃ and extracted 3× with DCM. The extracts were dried over Na₂SO₄, filtered and concentrated.

Step 2: 3-(1,3-oxazol-5-yl)-7-phenylimidazo[1,2-a]pyridine (7-2)

7-Phenylimidazo[1,2-a]pyridine-3-carbaldehyde (7-1, 0.030 g, 0.14 mmol), tosylmethyl isocyanide (0.032 g, 0.16 mmol) and K₂CO₃ (0.022 g, 0.16 mmol) were dissolved in 1 ml MeOH and the resulting solution was heated to reflux. After 4 h the reaction was quenched by the addition of water. The resulting mixture was extracted 3× with EtOAc, and the combined extracts were dried over Na₂SO₄, filtered and concentrated. The residue was purified by flash column chromatography, eluting with a gradient of DCM to 95:5 DCM/MeOH. The product was further purified by reverse phase preparative HPLC to afford the title compound. ¹H NMR (CDCl₃) δ 8.63 (d, 1H, J=7.1 Hz), 8.52 (s, 1H), 8.27 (s, 1H), 8.25 (s, 1H), 7.78 (m, 2H), 7.74 (dd, 1H, J=1.4, 7.3 Hz), 7.67 (s, 1H), 7.58 (m, 3H). LCMS m/z (M+1) Calc: 262.1, found 262.2.

What is claimed is:

1. A compound of Formula I:

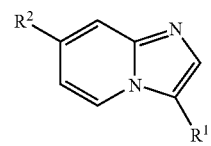

or a pharmaceutically acceptable salt or stereoisomer thereof, wherein a is 0 or 1;
b is 0 or 1;
m is 0, 1, or 2;
$R^1$ is selected from:
  1) aryl,
  2) $C_3$–$C_5$ cycloalkyl;
  3) $C_2$–$C_3$ alkenyl;
  4) $C_2$–$C_3$ alkynyl and
  5) heteroaryl,
said aryl, cycloalkyl and heteroaryl is optionally substituted with one or more substituents selected from $R^3$;
$R^2$ is selected from:
  1) aryl,
  2) $C_3$–$C_8$ cycloalkyl and
  3) heterocyclyl,
said aryl, cycloalkyl and heterocyclyl is optionally substituted with one or more substituents selected from $R^4$;
$R^3$ is:
  1) $(C=O)_aO_bC_1$–$C_3$ alkyl,
  2) $CO_2H$,
  3) halo,
  4) CN,
  5) OH,
  6) $O_bC_1$–$C_3$ perfluoroalkyl,
  7) $O_a(C=O)_bNH_2$,
  8) oxo,
  9) CHO, or
  10) $(N=O)H_2$;
$R^4$ is:
  1) $(C=O)_aO_bC_1$–$C_{10}$ alkyl,
  2) $(C=O)_aO_b$aryl,
  3) $C_2$–$C_{10}$ alkenyl, 4) $C_2$–$C_{10}$ alkynyl,
5) $(C=O)_aO_b$ heterocyclyl,
6) $CO_2H$,
7) halo,
8) CN,
9) OH,
10) $O_bC_1$–$C_6$ perfluoroalkyl,
11) $O_a(C=O)_bNR^6R^7$,
12) oxo,
13) CHO,
14) $(N=O)R^6R^7$, or
15) $(C=O)_aO_bC_3$–$C_8$ cycloalkyl,
said alkyl, aryl, alkenyl, alkynyl, heterocyclyl, and cycloalkyl optionally substituted with one or more substituents selected from $R^5$;

$R^5$ is selected from:
1) $(C=O)_rO_s(C_1$–$C_{10})$alkyl, wherein r and s are independently 0 or 1,
2) $O_r(C_1$–$C_3)$perfluoroalkyl, wherein r is 0 or 1,
3) $(C_0$–$C_6)$alkylene-$S(O)_mR^a$, wherein m is 0, 1, or 2,
4) oxo,
5) OH,
6) halo,
7) CN,
8) $(C_2$–$C_{10})$alkenyl,
9) $(C_2$–$C_{10})$alkynyl,
10) $(C_3$–$C_6)$cycloalkyl,
11) $(C_0$–$C_6)$alkylene-aryl,
12) $(C_0$–$C_6)$alkylene-heterocyclyl,
13) $(C_0$–$C_6)$alkylene-$N(R^b)_2$,
14) $C(O)R^a$,
15) $(C_0$–$C_6)$alkylene-$CO_2R^a$,
16) $C(O)H$, and
17) $(C_0$–$C_6)$alkylene-$CO_2H$,
said alkyl, alkenyl, alkynyl, cycloalkyl, aryl, and heterocyclyl is optionally substituted with up to three substituents selected from $R^b$, OH, $(C_1$–$C_6)$alkoxy, halogen, $CO_2H$, CN, $O(C=O)C_1$–$C_6$ alkyl, oxo, and $N(R^b)_2$;

$R^6$ and $R^7$ are independently selected from:
1) H,
2) $(C=O)O_bC_1$–$C_{10}$ alkyl,
3) $(C=O)O_bC_3$–$C_8$ cycloalkyl,
4) $(C=O)O_b$aryl,
5) $(C=O)O_b$heterocyclyl,
6) $C_1$–$C_{10}$ alkyl,
7) aryl,
8) $C_2$–$C_{10}$ alkenyl,
9) $C_2$–$C_{10}$ alkynyl,
10) heterocyclyl,
11) $C_3$–$C_8$ cycloalkyl,
12) $SO_2R^a$, and
13) $(C=O)NR^b{}_2$,
said alkyl, cycloalkyl, aryl, heterocylyl, alkenyl, and alkynyl is optionally substituted with one or more substituents selected from $R^5$, or $R^6$ and $R^7$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^5$;

$R^a$ is $(C_1$–$C_6)$alkyl, $(C_3$–$C_6)$cycloalkyl, aryl, or heterocyclyl; and $R^b$ is H, $(C_1$–$C_6)$alkyl, aryl, heterocyclyl, $(C_3$–$C_6)$cycloalkyl, $(C=O)OC_1$–$C_6$ alkyl, $(C=O)C_1$–$C_6$ alkyl or $S(O)_2R^a$.

2. The compound according to claim 1 of the Formula I, or a pharmaceutically acceptable salt or stereoisomer thereof,
wherein:
a is 0 or 1;
b is 0 or 1;
m is 0, 1, or 2;
$R^1$ is selected from: phenyl, thienyl, pyridyl, cyclopropyl and cyclobutyl; said phenyl, thienyl and pyridyl is optionally substituted with one or two substituents selected from $R^3$;
$R^2$ is selected from:
1) aryl,
2) $C_3$–$C_8$ cycloalkyl and
3) heterocyclyl,
said aryl, cycloalkyl and heterocyclyl is optionally substituted with one or more substituents selected from $R^4$;
$R^3$ is:
1) $(C=O)_aO_bC_1$–$C_3$ alkyl,
2) $CO_2H$,
3) halo,
4) CN,
5) OH,
6) $O_bC_1$–$C_3$ perfluoroalkyl,
7) $O_a(C=O)_bNH_2$,
8) oxo,
9) CHO, or
10) $(N=O)H_2$;

$R^4$ is:
1) $(C=O)_aO_bC_1$–$C_{10}$ alkyl,
2) $(C=O)_aO_b$aryl,
3) $C_2$–$C_{10}$ alkenyl,
4) $C_2$–$C_{10}$ alkynyl,
5) $(C=O)_aO_b$ heterocyclyl,
6) $CO_2H$,
7) halo,
8) CN,
9) OH,
10) $O_bC_1$–C6 perfluoroalkyl,
11) $O_a(C=O)_bNR^6R^7$,
12) oxo,
13) CHO,
14) $(N=O)^6R^7$, or
15) $(C=O)_aO_bC_3$–$C_8$ cycloalkyl,
said alkyl, aryl, alkenyl, alkynyl, heterocyclyl, and cycloalkyl optionally substituted with one or more substituents selected from $R^5$;

$R^5$ is selected from:
1) $(C=O)_rO_s(C_1$–$C_{10})$alkyl, wherein r and s are independently 0 or 1,
2) $O_r(C_1$–$C_3)$perfluoroalkyl, wherein r is 0 or 1,
3) $(C_0$–$C_6)$alkylene-$S(O)_mR^a$, wherein m is 0, 1, or 2,
4) oxo,
5) OH,
6) halo,
7) CN,
8) $(C_2$–$C_{10})$alkenyl,
9) $(C_2$–$C_{10})$alkynyl,
10) $(C_3$–$C_6)$cycloalkyl,
11) $(C_0$–$C_6)$alkylene-aryl,
12) $(C_0$–$C_6)$alkylene-heterocyclyl,
13) $(C_0$–$C_6)$alkylene-$N(R^b)_2$,
14) $C(O)R^a$,
15) $(C_0$–$C_6)$alkylene-$CO_2R^a$, 16) C(O)H, and
17) (C₀–C₆)alkylene-CO₂H,
said alkyl, alkenyl, alkynyl, cycloalkyl, aryl, and heterocyclyl is optionally substituted with up to three substituents selected from R$^b$, OH, (C₁–C₆)alkoxy, halogen, CO₂H, CN, O(C=O)C₁–C₆ alkyl, oxo, and N(R$^b$)₂;

R⁶ and R⁷ are independently selected from:
1) H,
2) (C=O)O$_b$C₁–C₁₀ alkyl,
3) (C=O)O$_b$C₃–C₈ cycloalkyl,
4) (C=O)O$_b$aryl,
5) (C=O)O$_b$heterocyclyl,
6) C₁–C₁₀ alkyl,
7) aryl,
8) C₂–C₁₀ alkenyl,
9) C₂–C₁₀ alkynyl,
10) heterocyclyl,
11) C₃–C₈ cycloalkyl,
12) SO₂R$^a$, and
13) (C=O)NR$^b$₂, said alkyl, cycloalkyl, aryl, heterocylyl, alkenyl, and alkynyl is optionally substituted with one or more substituents selected from R⁵, or R⁶ and R⁷ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from R⁵;

R$^a$ is (C₁–C₆)alkyl, (C₃–C₆)cycloalkyl, aryl, or heterocyclyl; and

R$^b$ is H, (C₁–C₆)alkyl, aryl, heterocyclyl, (C₃–C₆)cycloalkyl, (C=O)OC₁–C₆ alkyl, (C=O)C₁–C₆ alkyl or S(O)₂R$^a$.

3. The compound according to claim 2, or a pharmaceutically acceptable salt or stereoisomer thereof, wherein
R¹ is selected from phenyl and pyridyl, optionally substituted with one or more substituents selected from R³; and
R² is selected from phenyl, pyridyl and 1,2-dihydropyridinyl, optionally substituted with one to three substituents selected from R⁴.

4. The compound according to claim 1 selected from:
3,7-diphenylimidazo[1,2-a]pyridine
7-phenyl-3-pyridin-4-ylimidazo[1,2-a]pyridine
7-phenyl-3-pyridin-3-ylimidazo[1,2-a]pyridine
[4-(3-phenylimidazo[1,2-a]pyridin-7-yl)phenyl]methanol
7-(4-{[4-(methylsulfonyl)piperazin-1-yl]methyl}phenyl)-3-phenylimidazo[1,2-a]pyridine
4-methyl-1-[4-(3-phenylimidazo[1,2-a]pyridin-7-yl)benzyl]-1,4-diazepan-5-one
7-{4-[(4-acetylpiperazin-1-yl)methyl]phenyl}-3-phenylimidazo[1,2-a]pyridine
N-methyl-4-[4-(3-phenylimidazo[1,2-a]pyridin-7-yl)benzyl]piperazine-1-carboxamide
4-[4-(3-phenylimidazo[1,2-a]pyridin-7-yl)benzyl]piperazine-1-carboxamide
1-[4-(3-phenylimidazo[1,2-a]pyridin-7-yl)benzyl]-1,4-diazepan-5-one
7-(4-{[4-(methylsulfonyl)piperidin-1-yl]methyl}phenyl)-3-phenylimidazo[1,2-a]pyridine
3-phenyl-7-(4-pyridyl)imidazo[1,2-a]pyridine
7-(1-oxy-pyridin-4-yl)-3-phenyl-imidazo[1,2-a]pyridine
4-(3-phenyl-imidazo[1,2-a]pyridin-7-yl)-1H-pyridin-2-one
3-(6-methoxypyridin-2-yl)-7-phenylimidazo[1,2-a]pyridine
6-(7-phenylimidazo[1,2-a]pyridine-3-yl)pyridine-2(1H)-one
3-(6-methoxypyridin-3-yl)-7-phenylimidazo[1,2-a]pyridine
7-phenyl-3-(1,3-thiazol-2-yl)imidazo[1,2-a]pyridine
4-(3-phenylimidazo[1,2-a]pyridine-7-yl)-1-(3-piperidin-1-ylpropyl)pyridine-2(1H)-one
1-[3-(4-methylpiperazin-1-yl)propyl]-4-(3-phenylimidazo[1,2-a]pyridine-7-yl)pyridine-2(1H)-one
1-(3-hydroxypropyl)-4-(3-phenylimidazo[1,2-a]pyridine-7-yl)pyridine-2(1H)-one
1-(3-morpholin-4-ylpropyl)-4-(3-phenylimidazo[1,2-a]pyridin-2(1H)-one
1-(3,3-diethoxypropyl)-4-(3-phenylimidazo[1,2-a]pyridine-2(1H)-one
1-(3-{3-[(dimethylamino)methyl]piperidin-1-yl}propyl)-4-(3-phenylimidazo[1,2-a]pyridine-7-yl)pyridine-2(1H)-one
7-phenyl-3-(1,3-thiazol-5-yl)imidazo[1,2-a]pyridine
3-(1,3-oxazol-5-yl)-7-phenylimidazo[1,2-a]pyridine
or a pharmaceutical acceptable salt thereof.

5. A pharmaceutical composition which is comprised of a therapeutically effective amount of a compound in accordance with claim 1 and a pharmaceutically acceptable carrier.

6. A pharmaceutical composition made by combining a therapeutically effective amount of the compound of claim 1 and a pharmaceutically acceptable carrier.

7. A method of treating acute myeloid leukemia which comprises administering a therapeutically effective amount of a compound of claim 1.

* * * * *